United States Patent
Kang et al.

(10) Patent No.: US 11,786,549 B2
(45) Date of Patent: Oct. 17, 2023

(54) ANTI-INFLAMMATORY COMPOSITION COMPRISING GRAPHENE NANO-STRUCTURE

(71) Applicants: SEOUL NATIONAL UNIVERSITY R&DB FOUNDATION, Seoul (KR); BIOGRAPHENE INC., Seoul (KR)

(72) Inventors: Kyung-Sun Kang, Seoul (KR); Byung-Chul Lee, Seoul (KR); Jin Young Lee, Seoul (KR); Jong Bo Park, Seoul (KR)

(73) Assignees: SEOUL NATIONAL UNIVERSITY R&DB FOUNDATION, Seoul (KR); BIOGRAPHENE INC., Seoul (KR)

( * ) Notice: Subject to any disclaimer, the term of this patent is extended or adjusted under 35 U.S.C. 154(b) by 0 days.

(21) Appl. No.: 16/766,514

(22) PCT Filed: Nov. 23, 2018

(86) PCT No.: PCT/KR2018/014557
§ 371 (c)(1),
(2) Date: May 22, 2020

(65) Prior Publication Data
US 2020/0360429 A1  Nov. 19, 2020

(30) Foreign Application Priority Data
Nov. 24, 2017  (KR) .................. 10-2017-0158752
Nov. 24, 2017  (KR) .................. 10-2017-0158753

(51) Int. Cl.
*A61K 33/44* (2006.01)
*A61P 37/06* (2006.01)
*A61K 9/16* (2006.01)

(52) U.S. Cl.
CPC .............. *A61K 33/44* (2013.01); *A61K 9/16* (2013.01); *A61P 37/06* (2018.01)

(58) Field of Classification Search
CPC ............ A61K 33/44; A61K 9/16; A61P 37/06
See application file for complete search history.

(56) References Cited

U.S. PATENT DOCUMENTS

| 2013/0216581 | A1  | 8/2013 | Fahmy et al. |
| 2016/0193249 | A1* | 7/2016 | Tour .................. A61P 5/14 424/489 |

FOREIGN PATENT DOCUMENTS

| CN | 106470706 A | 3/2017 |
| EP | 3 130 353 A1 | 2/2017 |

(Continued)

OTHER PUBLICATIONS

Shen, S.et al., 2020, Graphene quantum dots with high yield and high quality synthesized from low cost precursor of aphanitic graphite., MDPI, Nanomaterials, 10, 375 (Year: 2020).*

(Continued)

*Primary Examiner* — Bethany P Barham
*Assistant Examiner* — Ayaan A Alam
(74) *Attorney, Agent, or Firm* — Vorys, Sater, Seymour and Pease LLP; Mih Suhn Koh

(57) ABSTRACT

The present invention relates to an anti-inflammatory composition comprising a graphene nano-structure as an active ingredient. Specifically, the present invention relates to a pharmaceutical composition for preventing or treating an inflammatory disease, and a cosmetic composition or feed composition for preventing or improving an inflammatory disease, which include the anti-inflammatory composition, and a method of treating an inflammatory disease, including administering the composition to a subject in need thereof.

5 Claims, 21 Drawing Sheets

(56) References Cited

FOREIGN PATENT DOCUMENTS

| JP | 2015-524793 A | 8/2015 |
| JP | 2016-529310 A | 9/2016 |
| JP | 2016-540033 A | 12/2016 |
| KR | 10-2015-0115671 A | 10/2015 |
| WO | 2015/034930 A1 | 3/2015 |

OTHER PUBLICATIONS

Crohn's disease, 2020, Mayo Clinic, screenshot of https://www.mayoclinic.org/diseases-conditions/crohns-disease/symptoms-causes/syc-20353304 (Year: 2020).*

The George Washington University Hospital, Colitis, 2021, screenshot from https://www.gwhospital.com/conditions-services/digestive-disorder-center/colitis (Year: 2021).*

Yang, H., et al., Engineering the shape of block copolymer particles by surface-modulated graphene quantum dots, 2015, Chemistry of Materials, 28, 830-837 (Year: 2015).*

Qin et al., "Graphene quantum dots induce apoptosis, autophagy, and inflammatory response via p38 mitogen-activated protein kinase and nuclear factor-KB mediated signaling pathways in activated THP-1 macrophages", Toxicology, 2015, vol. 327, pp. 62-76.

Tosic et al., "Graphene quantum dots show protective effect on a model of experimental autoimmune encephalomyelitis", European Neuropsychopharmacology, Oct. 2016, vol. 26, supplement 2, P.1.f.007, pp. S211-S212.

Zhou et al., "Graphene functionalized scaffolds reduce the inflammatory 1-13 response and supports endogenous neuroblast migration when implanted in the adult brain", PLoS One, Mar. 15, 2016, vol. 11(3), e0151589.

Notice of Reasons for Refusal for corresponding JP Patent Application No. 2020-546263, dated Apr. 22, 2021, fourteen pages.

Extended European Search Report dated Jul. 2, 2021, for corresponding EP Patent Application No. 18881388.5, 7 pages.

Lee et al., "Graphene quantum dots as anti-inflammatory therapy for colitis", Sci. Adv., 2020, vol. 6, No. 18, eaaz2630, 13 pages.

Chinese Office Action for corresponding application CN 201880075667.4, dated Oct. 26, 2021, 6 pages.

Qin et al., "Graphene quantum dots induce apoptosis, autophagy, and inflammatory response via p38 mitogen-activated protein kinase and nuclear factor-kappaB mediated signaling pathways in activated THP-1 macrophages", Toxicology, xxx, (2015), pp. 62-76.

Ou et al., "Toxicity of graphene-family nanoparticles: a general review of the origins and mechanisms", Particle and Fibre Toxicology, (2016), 13:57, 24 pages.

Ozeki et al., "Asymptomatic colitis induced by low-dose methotrexate", BMJ Case Rep, published online, 2016, 3 pages, doi: 10.1136/bcr-2016-217771.

Freeman, "Colitis associated with biological agents", World J Gastroenterol, 2012, 18(16): 1871-1874.

* cited by examiner

ANTI-INFLAMMATORY COMPOSITION COMPRISING GRAPHENE NANO-STRUCTURE

CROSS-REFERENCE TO RELATED APPLICATIONS

This application is a 371 of PCT/KR2018/014557, filed Nov. 23, 2018, which claims the benefit of priority from Korean Patent Application No. 10-2017-0158752, filed Nov. 24, 2017 and Korean Patent Application No. 10-2017-0158753, filed Nov. 24, 2017, the contents of each of which are incorporated herein by reference in its entirety.

TECHNICAL FIELD

The present invention relates to an anti-inflammatory composition comprising a graphene nano-structure as an active ingredient. Particularly, the present invention relates to a pharmaceutical composition for preventing or treating an inflammatory disease, which comprises the composition, a cosmetic composition or feed composition for preventing or improving an inflammatory disease, and a method of preventing or treating an inflammatory disease using the composition.

BACKGROUND ART

Inflammation is a defensive response of biological tissue against tissue damage, external stimuli or various infectious sources, and a combined pathological phenomenon generated by an organic interaction between various inflammation-mediated factors and various immune cells in blood vessels and body fluids. In one example, when an external stimulus is applied to cells, proinflammatory cytokines such as tumor necrosis factor-alpha (TNF-α) or interleukin-6 (IL-6) increase, and the cytokines stimulate the expression of a gene such as inducible nitric oxide synthase (iNOS) or cyclooxygenase-2 (COX-2), thereby producing nitric oxide (NO) or prostaglandin E2 (PGE2), resulting in an inflammatory response. A cytokine such as IL-6, IL-8, TNF-α or IFN-α, which is associated with the immune response, may be synthesized and secreted by a macrophage, and the expression mediated by a macrophage may be unregulated or downregulated according to the type of cytokine (Cavaillon J M, Biomed. Pharmacother. 1994;48(10):445-53).

NO has various physiologically active functions such as a defense function, a signal transmission function, neurotoxicity and vasodilation in the body, but NO excessively produced by iNOS in an inflammatory state causes vascular permeability, edema, tissue damage, genetic mutation and nerve damage. Accordingly, many studies have been conducted to develop a material for inhibiting the excessive production of NO, and it has been reported that phenylpropanoid compounds such as caffeic acid, chlorogenic acid, cinnamic acid, p-coumaric acid, hesperidin and rosmarinic acid derived from various natural substances can inhibit skin inflammation (Japanese Unexamined Patent Application No. 2000-319154). However, research on natural substance-derived ingredients is still its infancy, and the development of more diverse ingredients is required.

Among various inflammatory diseases, inflammatory bowel disease (IBD) represented by Crohn's disease and ulcerative colitis refers to a chronic inflammatory disease whose cause of invasion of the gastrointestinal tract is not exactly known. Broadly, the IBD is classified into two types such as Crohn's disease and ulcerative colitis, but may also include intestinal Behcet's disease. IBD is more often found in Caucasians or Jews than Blacks or Asians, but cases occurring in Asians are gradually increasing. An affected age ranges from 15 to 35, and symptoms of ulcerative colitis are generally diarrhea (bloody and mucous-like stool), tenesmus, abdominal pain, abdominal tenderness, and the loss of body weight, and symptoms of Crohn's disease include a body weight loss, lower right abdomen pain, an abnormal anus, and abdominal tenderness. The intestinal Behcet's disease has symptoms such as diarrhea and abdominal pain, similar to those symptoms, and is accompanied by other symptoms similar to Behcet's disease.

Internal treatment is a principle, but when it is difficult to provide or complications occur, surgical treatment is provided. Although drug treatment is being provided, since the cause has not been clearly identified, no effective therapeutic agent was developed, and thus general anti-inflammatory drugs, adrenal cortical hormones, immunosuppressive agents, antibiotics and other drugs are used in combination. The type or amount of a drug is adjusted according to the type, degree, lesion or complications of inflammation for use. However, such a combination therapy has a disadvantage of high possibility of side effects. Therefore, the development of an effective therapeutic agent for treating inflammatory bowel disease is very important.

Thus, as a result of diligent research to discover graphene derivatives having activity as a biomedical therapeutic agent, the inventors confirmed that a graphene nano-structure, particularly, nano-sized graphene whose particle size and form are adjusted, inhibits the expression of an inflammatory factor and/or the secretion of an inflammatory cytokine, and has an anti-inflammatory activity inducing differentiation of macrophages into specific subtypes, and thus the present invention was completed.

[Disclosure]

Technical Problem

The present invention is directed to providing an anti-inflammatory composition, which comprises a graphene nano-structure as an active ingredient.

The present invention is also directed to providing a method of preventing or treating an inflammatory disease, which comprises administering the composition to a subject in need of the composition.

Technical Solution

In one aspect, the present invention provides an anti-inflammatory composition, which comprises a graphene nano-structure as an active ingredient.

The present invention is based on the findings that a graphene nano-structure, particularly, a nano-sized graphene whose particle size and form are adjusted inhibits the expression of an inflammatory factor and/or the secretion of an inflammatory cytokine, induces the differentiation of macrophages into specific subtypes, thereby exhibiting an anti-inflammatory effect, and can effectively prevent or treat, particularly, inflammatory bowel disease, through animal testing.

In the present invention, the graphene nano-structure refers to a nano-sized graphene derivative, which comprises nano-sized graphene oxide (nano-GO) and a graphene quantum dot (GQD).

The term "graphene" used herein refers to a polycyclic aromatic molecule formed by linking a plurality of carbon atoms using covalent bonds, wherein the carbon atoms linked using the covalent bonds are a basic repeat unit, which makes it possible to form a 6-membered ring, but to even form a 5-membered ring and/or a 7-membered ring.

The term "oxidized graphene" may refer to graphene oxide, abbreviated as "GO." On the graphene, a structure to which a functional group containing an oxygen atom such as a carboxyl group, a hydroxyl group or an epoxy group binds may be comprised, but the present invention is not limited thereto.

The term "nano-sized graphene oxide (nano-GO)" refers to graphene oxide prepared in the form of a particle with a nanometer-scale size, and may comprise, on graphene, a structure to which a functional group containing an oxygen atom such as a carboxyl group, a hydroxyl group or an epoxy group binds, but the present invention is not limited thereto. The nano-GO may refer to plate-shaped particles having a predetermined thickness of 12 nm or less and an average diameter of approximately 15 to 50 nm. For example, the nano-GO may be prepared by applying ultrasonic waves to graphene oxide (e.g., by tip-sonification), but the present invention is not limited thereto. For example, the nano-GO may have an average diameter of 15 to 45 nm, 15 to 27 nm, 25 to 35 nm, 35 to 45 nm, or 25 to 45 nm. Further, the nanoparticles may be particles with a thickness of 5 to 12 nm, 3 to 9 nm, 3 to 7 nm, 5 to 9 nm, or 5 to 7 nm, but the present invention is not limited thereto.

The term "graphene quantum dot (GQD)" refers to graphene having a nano-sized fragment, and the GQD may be a graphene particle having several nm-scale width, length and height, prepared by a suitable process. The GQD may be obtained by thermo-oxidative cutting of a carbon fiber, but a method of preparing the same is not limited to the above-described method. For example, the GQD may be a particle having an average diameter of 1 to 5 nm and a thickness of 0.5 to 3 nm, but the present invention is not limited thereto. For example, the GQD may have an average diameter of 1 to 3 nm or 3 to 5 nm. Further, the GQD may have a height of 0.5 to 2.5 nm, 0.5 to 1.5 nm, or 1.5 to 2.5 nm.

The term "anti-inflammation" used herein refers to an action of inhibiting or reducing inflammation, and the term "inflammation" is a defensive response occurring in the body when living tissue is damaged, and a cause of an inflammatory disease.

In the present invention, the anti-inflammatory composition exhibits an activity of inhibiting or reducing inflammation, and thus can be used for prevention, treatment or improvement of an inflammatory disease.

Specifically, the composition containing the graphene nano-structure of the present invention may inhibit or reduce inflammation by inhibiting the expression or secretion of a proinflammatory cytokine, inhibiting myeloperoxidase (MPO) activity, inhibiting Th1 proliferation, differentiation or the Th1 response, promoting inhibitory T cell activity or upregulating M2b macrophages.

For example, the secretion or expression of downstream cytokines of representative proinflammatory cytokines, such as IFNγ, TNF, IL-6 and/or MCP-1, or MPO activity may be reduced by treating the composition of the present invention, indicating that the migration of neutrophils and inflammation may be inhibited. Further, the differentiation into Th1 cells known to play an important role in enterocolitis and/or the proliferation of the Th1 cells is/are inhibited, and the expression of a gene specific for the Th1 cells may also be reduced. Further, inflammation may be relieved by converting M1 macrophages to M2 types during an inflammatory response. Particularly, among M2 subtypes, M2b macrophages may be unregulated, thereby attenuating an inflammatory response.

The "expression" includes both gene expression and protein expression.

The inflammatory disease refers to a disease caused by inflammation, and the anti-inflammatory composition of the present invention may be used in prevention or treatment of an inflammatory disease.

The inflammatory disease is not particularly limited as long as it may be alleviated, reduced, improved or treated by the pharmaceutical composition of the present invention, and may be, for example, erythema, atopy, rheumatoid arthritis, Hashimoto's thyroiditis, malignant anemia, Addison's disease, Type I diabetes, lupus, chronic fatigue syndrome, fibromyalgia, hypothyroidism, hyperthyroidism, scleroderma, Behcet's disease, an inflammatory bowel disease, multiple sclerosis, myasthenia gravis, Meniere's syndrome, Guillain-Barre syndrome, Sjogren's syndrome, vitiligo, endometriosis, psoriasis, or systemic scleroderma, but the present invention is not limited thereto.

Specifically, an inflammatory disease that can be treated by the pharmaceutical composition including the graphene nano-structure according to the present invention may be inflammatory bowel disease. The inflammatory bowel disease may be chronic enteric inflammation caused by an unknown reason, and usually refers to idiopathic inflammatory bowel disease such as ulcerative colitis, Crohn's disease, and intestinal Behcet's disease. In a broader sense, the inflammatory bowel disease may include all of enteric inflammatory diseases, for example, infectious enterocolitis such as bacterial, viral, amoebic and intestinal tuberculosis, ischemic bowel disease, and radiation enterocolitis. The composition of the present invention may be used in prevention or treatment of inflammatory diseases occurring in both intestines, for example, inflammatory bowel disease in the broader sense, for example, infectious enterocolitis such as bacterial, viral, amoebic and intestinal tuberculosis, ischemic bowel disease, and radiation enterocolitis, preferably, Crohn's disease, ulcerative colitis and intestinal Behcet's disease, without limitation.

Symptoms of the inflammatory bowel disease vary according to a specific disease, and generally, symptoms such as abdominal pain, discomfort in the lower abdomen, shortening of the colon, hair loss, decreased activity, weight loss, an increased bleeding index (bleeding) or an increased defecation index (diarrhea) may be exhibited. Even the same disease may show a different pattern according to the range, location or severity of a lesion.

The prevention or treatment of the inflammatory disease may be performed by reducing an increase in the secretion of inflammatory cytokine IL-23 or TGF-β and/or the expression of a gene related thereto.

IL-23 is a heterodimer cytokine, which plays a critical role in an immune response. IL-23 is produced from dendritic cells, macrophages and other immune cells, is considered as a critical factor affecting the balance between resistance and immunity in the intestines, and confirmed as mediating inflammation in the colon. TGF-β is a factor synthesized in various types of tissue, and synergistically acts with TGF-α. TGF-β is known to play a critical role in embryonic development, cell differentiation, hormone secretion and immune function. Particularly, TGF-β is known to cause an inflammatory response.

The term "prevention" used herein refers to all actions of inhibiting or delaying an inflammatory disease by administration of the composition.

The term "treatment" used herein refers to all actions involved in alleviating or beneficially changing the symptoms of an inflammatory disease by administration of the composition.

The pharmaceutical composition according to the present invention may further include a pharmaceutically acceptable carrier. The term "pharmaceutically acceptable" used herein means exhibiting non-toxic properties in cells or a human exposed to the composition. The carrier may be any one known in the art, such as a buffer, a preservative, an analgesic, a solubilizer, an isotonic agent, a stabilizer, a base, an excipient or a lubricant, without limitation. The carrier, excipient and diluent that can be included in the pharmaceutical composition of the present invention may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, poylvinylpyrrolidone, water, methylhydroxy benzoate, propylhydroxy benzoate, talc, magnesium stearate and mineral oil. In preparation, the composition may be formulated with a diluent or an excipient such as a filler, a thickening agent, a binder, a wetting agent, a disintegrant, a surfactant, which are conventionally used. Typically, a surfactant that can be used to facilitate transmembrane migration is derived from a steroid, or a cationic lipid such as N-[1-(2,3-dioleoyl)propyl-N,N,N-trimethylammonium chloride] (DOTMA), or cholesterol hemisuccinate.

In another aspect, the present invention provides a method of preventing or treating an inflammatory disease, which comprises administering the pharmaceutical composition to a subject in need of the composition.

The term "subject" used herein includes all animals including a human in which an inflammatory disease may occur or is likely to occur, and the inflammatory disease may be effectively prevented or treated by administering the pharmaceutical composition of the present invention into a subject. The pharmaceutical composition of the present invention may be administered in combination with a conventional inflammatory disease therapeutic agent.

The term "administration" used herein refers to introduction of a predetermined material to a patient by a suitable method, and the administration route of the composition may be any general route that can reach desired tissue. The administration may be intraperitoneal administration, intravenous administration, intramuscular administration, subcutaneous administration, intradermal administration, oral administration, topical administration, intranasal administration, intrapulmonary administration or intrarectal administration, but the present invention is not limited thereto. A solid formulation for oral administration may be a tablet, pill, powder, granule or capsule, and such a solid formulation may be prepared by mixing at least one excipient, for example, starch, calcium carbonate, sucrose, lactose and gelatin, with the active ingredient. Also, in addition to the simple excipient, lubricants such as magnesium stearate and talc may also be used. As a liquid formulation for oral administration, a suspension, a liquid for internal use, an emulsion, or a syrup may be used, and a generally-used simple diluent such as water or liquid paraffin, as well as various types of excipients, for example, a wetting agent, a sweetener, a flavor and a preservative may be included. However, in oral administration, since a peptide is easily digested, an oral composition is preferably formulated to coat an active drug or protect the peptide from being degraded in the stomach. A formulation for parenteral administration includes a sterilized aqueous solution, a non-aqueous solvent, a suspension, an emulsion, a lyophilizing agent and a suppository. As the non-aqueous solvent or suspension, propylene glycol, polyethylene glycol, vegetable oil such as olive oil, or an injectable ester such as ethyl oleate may be used. As a suppository base, Witepsol, Macrogol, Tween 61, cacao butter, laurin butter, or glycerogelatin may be used. To increase the stability or absorbability of a peptide, carbohydrates such as glucose, sucrose, dextran, etc., antioxidants such as ascorbic acid, glutathione, etc., chelating materials, low molecular proteins, or different stabilizers may be used.

In addition, the pharmaceutical composition of the present invention may be administered by any device that can allow an active material to be transported to target cells. Preferable administration methods and agents include an intravenous injection, a subcutaneous injection, an intradermal injection, an intramuscular injection, and infusion. An injection may be prepared using an aqueous solvent such as physiological saline or a Ringer's solution, or a non-aqueous solvent such as vegetable oil, a higher fatty acid ester (e.g., ethyl oleate) or an alcohol (e.g., ethanol, benzyl alcohol, propylene glycol or glycerin), and a pharmaceutical carrier such as a stabilizer for preventing deterioration (e.g., ascorbic acid, sodium hydrogen sulfite, sodium pyrosulfite, BHA, tocopherol or EDTA), an emulsifier, a buffer for adjusting pH, or a preservative for suppressing microbial growth (e.g., phenyl mercury nitrate, thimerosal, benzalkonium chloride, phenol, cresol or benzyl alcohol).

Meanwhile, the pharmaceutical composition of the present invention is administered at a pharmaceutically acceptable amount. The term "pharmaceutically acceptable amount" refers to an amount sufficient for treating a disease at a reasonable benefit/risk ratio applicable for medical treatment and not generating side effects, and an effective dosage may be easily determined by those of ordinary skill in the art according to parameters including a patient's gender, age, body weight and health condition, a type of disease, severity, drug activity, sensitivity to a drug, an administration method, an administration time, an administration route, an excretion rate, a treatment duration, combination or drugs simultaneously used, and other parameters well known in the medical field. Generally, an active ingredient may be administered at approximately 0.01 mg/kg/day to 1,000 mg/kg/day. For oral administration, the dosage is preferably approximately 50 to 500 mg/kg and the administration may be conducted once or more per day.

The composition of the present invention may be administered separately or in combination with other therapeutic agents, and may be sequentially or simultaneously administered with a conventional therapeutic agent, or administered in a single dose or multiple doses. In consideration of all of the above-mentioned parameters, it is important to achieve the maximum effect with the minimum dose without a side effect, and such a dose may be easily determined by one of ordinary skill in the art.

In addition, in the present invention, the anti-inflammatory composition may be a cosmetic composition for preventing or improving an inflammatory disease.

The cosmetic composition of the present invention may contain the graphene nano-structure of the present invention at 0.0001 to 50 wt %, and particularly, 0.01 wt % to 10 wt %, with respect to the total weight of the composition, but the present invention is not limited thereto. The cosmetic composition shows an excellent effect of the present invention within the above range, and stabilizes the formulation of the composition.

The cosmetic composition of the present invention may be prepared in a formulation selected from the group consisting of a solution, an ointment for external use, a cream, a foam, a nourishing toner, a softening toner, a pack, an emulsion, a makeup base, an essence, a soap, a liquid detergent, a bath preparation, a sun screen cream, a sun screen oil, a suspension, a paste, a gel, a lotion, a powder, a surfactant-containing cleanser, an oil, a powder foundation, an emulsion foundation, a wax foundation, a patch and a spray, but the present invention is not limited thereto.

The cosmetic composition of the present invention may further comprise one or more of cosmetologically acceptable carriers formulated in a general skin cosmetic, and common components, for example, an oily component, water, a surfactant, a moisturizer, a low molecular alcohol, a thickener, a chelating agent, a coloring agent, a preservative and a fragrance may be suitably added, but the present invention is not limited thereto.

The cosmetologically acceptable carrier included in the cosmetic composition of the present invention may vary according to a formulation of the cosmetic composition.

When the formulation of the present invention is an ointment, a paste, a cream or a gel, as a carrier ingredient, animal oil, vegetable oil, a wax, paraffin, starch, tragacanth, a cellulose derivative, polyethylene glycol, silicone, bentonite, silica, talc or zinc oxide may be used, but the present invention is not limited thereto. These may be used alone or in combination of two or more thereof.

When the formulation of the present invention is a powder or spray, as a carrier ingredient, lactose, talc, silica, aluminum hydroxide, calcium silicate, or polyamide powder may be used, and particularly, when the formulation of the present invention is a spray, a propellant such as chlorofluorohydrocarbon, propane/butane or dimethyl ether may be further included, but the present invention is not limited thereto. These may be used alone or in combination of two or more thereof.

When the formulation of the present invention is a solution or emulsion, as a carrier ingredient, a solvent, a solubilizer or an emulsifier may be used. For example, the carrier ingredient may be water, ethanol, isopropanol, ethyl carbonate, ethyl acetate, benzyl alcohol, benzyl benzoate, propylene glycol or 1,3-butylglycol oil, and particularly, cottonseed oil, peanut oil, corn seed oil, olive oil, castor oil, sesame oil, glycerol fatty acid ester, or fatty acid ester of polyethylene glycol or sorbitan, but the present invention is not limited thereto. These may be used alone or in combination of two or more thereof.

When the formulation of the present invention is a suspension, as a carrier ingredient, a liquid diluent such as water, ethanol or propylene glycol, a suspending agent such as ethoxylated isostearyl alcohol, polyoxyethylene sorbitol ester or polyoxyethylene sorbitan ester, microcrystalline cellulose, aluminum metahydroxide, bentonite, agar or tragacanth may be used, but the present invention is not limited thereto. These may be used alone or in combination of two or more thereof.

When the formulation of the present invention is a soap, as a carrier ingredient, an alkali metal salt of a fatty acid, a hemiester salt of a fatty acid, a fatty acid protein hydrolysate, an isethionate, a lanolin derivative, an aliphatic alcohol, vegetable oil, glycerol or a saccharide may be used, but the present invention is not limited thereto. These may be used alone or in combination of two or more thereof.

When the formulation of the present invention is a surfactant-containing cleanser, as a carrier ingredient, an aliphatic alcohol sulfate, an aliphatic alcohol ether sulfate, monoester sulfosuccinate, isethionate, an imidazolium derivative, methyl taurate, sarcositate, fatty acid amide ether sulfate, alkylamidobetaine, an aliphatic alcohol, fatty acid glyceride, fatty acid diethanolamide, vegetable oil, a lanolin derivative or ethoxylated glycerol fatty acid ester may be used, but the present invention is not limited thereto. These may be used alone or in combination of two or more thereof.

Further, in the present invention, the anti-inflammatory composition may be a food additive or health functional food for preventing or improving an inflammatory disease. When the composition of the present invention is used as a food additive, the graphene nano-structure may be added alone or in combination with other foods or food ingredients, and may be suitably used according to a conventional method. A mixing amount of an active ingredient may be suitably determined according to the purpose of use (prevention, health or therapeutic treatment).

The term "health functional food" used herein refers to food which contains a specific component for health supplementation as a raw material or manufactured or processed by a method of extracting, concentrating, purifying or mixing a specific ingredient contained in a food ingredient, or a food designed and processed to sufficiently exert bioregulatory functions such as biophylaxis, biorhythm regulation or disease prevention and recovery by the ingredient in the living body, and the composition for health food may perform a function related to the prevention of and recovery from a disease.

In addition, there is no limitation on the type of health food in which the composition of the present invention can be used. In addition, the composition comprising the graphene nano-structure or a sitologically acceptable salt as an active ingredient may be prepared by adding appropriate other supplementary ingredients and known additives, which can be contained in health functional food according to the choice of one of ordinary skill in the art. Examples of food that can be added may include meat, sausage, bread, chocolate, candies, snacks, confectionary, pizza, ramen, other noodles, gums, dairy products including ice creams, all types of soup, beverages, teas, health drinks, alcoholic beverages and vitamin complexes, and the graphene nano-structure according to the present invention may be prepared by adding an extract, a tea, a jelly or a juice, produced of an extract as a main ingredient.

Further, in the present invention, the anti-inflammatory composition may be a feed composition for preventing or improving an inflammatory disease.

The term "feed" used herein is any natural or artificial diet, meal, or an ingredient of the meal, which is eaten, ingested or digested by an animal, and feed containing the graphene nano-structure of the present invention as an active ingredient can be manufactured in various forms known in the art, and preferably, concentrated feed, roughage and/or special feed may be included.

A content of the graphene nano-structure included in the feed composition of the present invention may vary according to the purpose of use and conditions for use of the feed, and for example, the graphene nano-structure may be contained at 0.01 to 100 wt %, and more specifically, 1 to 80 wt %, with respect to the total weight of a livestock feed composition, but the present invention is not limited thereto.

In still another aspect, the present invention provides a use of the graphene nano-structure for preventing or treating an inflammatory disease.

In yet another aspect, the present invention provides a composition comprising the graphene nano-structure to prevent or treat an inflammatory disease.

In yet another aspect, the present invention provides a use of the graphene nano-structure to prepare a drug for preventing or treating an inflammatory disease.

Detailed descriptions of the graphene nano-structure and the inflammatory disease are as described above.

The details described in the composition, treatment method and use of the present invention are applied equally unless they contradict each other.

Advantageous Effects

As a composition according to the present invention has a nano-sized graphene derivative, that is, a graphene nano-structure, it can inhibit the secretion and/or expression of a proinflammatory cytokine and regulate the differentiation of cells involved in an inflammatory response, and thus can be effectively used in treatment of an inflammatory disease, particularly, inflammatory bowel disease.

MODES OF THE INVENTION

Figure 1:
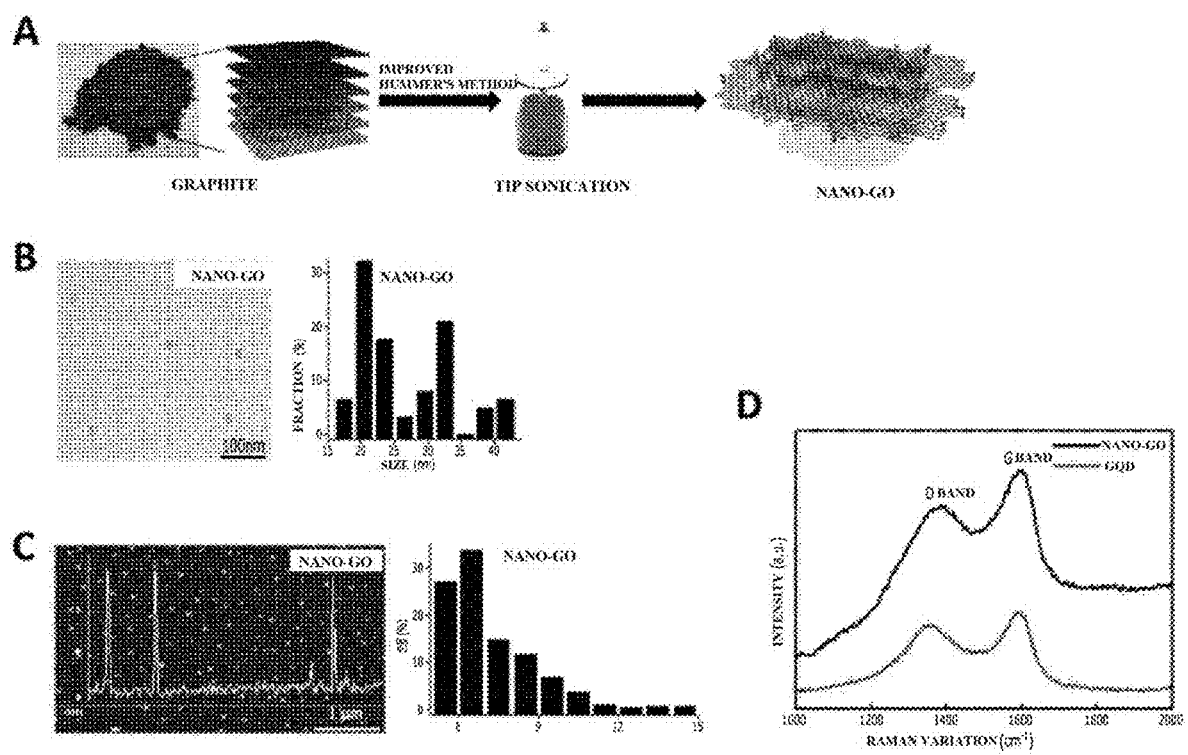
FIG. 1 shows a synthetic method and characteristics of nano-GOs. (A) schematically shows the synthetic method of nano-GOs according to the present invention. (B) shows a representative TEM image of nano-GOs according to the present invention and particle size distribution calculated therefrom. (C) shows a representative AFM image and a line profile analysis result of nano-GOs according to the present invention. (D) shows representative Raman spectra of nano-GOs according to the present invention.

Hereinafter, the configuration and effects of the present invention will be described in detail with reference to examples. These examples are merely provided to illustrate the present invention, and the scope of the present invention is not limited to these examples.

Preparation Example 1

Preparation and Biotinylation of Nano-GOs

Pristine graphene oxides (GOs) were synthesized by an improved Hummer's method. To prepare nano-sized GOs, a distilled water solution of the obtained GOs (3 mg/mL) was vigorously tip-sonicated for 3 hours, and vacuum-filtered using a cellulose nitrate membrane filter (0.45 μm, GE Healthcare).

In addition, nano-GOs were biotinylated by EDC coupling. First, 10 mg of N-(3-Dimethylaminopropyl)-N'-ethylcarbodiimide hydrochloride (EDC reagent, Sigma) was added to 10 mL of a nano-GO solution (3 mg/mL) to replace edge carboxyl groups with an EDC reagent. After 30 minutes, 20 mg of amine-$PEG_3$-biotin (Thermo Scientific) was added to the solution to allow a reaction for 24 hours, thereby forming an amide bond between the activated terminal of nano-GO and a reactive amide group of biotin. Similar to the nano-sized GO preparation method, the final product was obtained in powder form after appropriate dialysis and filtration steps.

Preparation Example 2

Preparation and Biotinylation of GQDs

GQDs were synthesized by thermo-oxidative cutting of carbon fibers (Carbon Make, South Korea) by a reaction in a 3:1 mixed solution of sulfuric acid and nitric acid (Samjeon Chemical Co., Ltd.) at 80° C. for 1 day. The solution was diluted and dialyzed using an MWCO 1 kD nitrocellulose membrane (Fisher Scientific) to remove very small fragments and the remaining acid, followed by vacuum-filtration with an inorganic membrane filter (Whatman-Anodisc 47, GE Healthcare). The final product was obtained in powder form by lyophilization.

In addition, GQDs were biotinylated by the same method as used for the nano-GO of Preparation Example 1, and the final product was obtained in powder form after suitable dialysis and filtration steps.

Experimental Example 1

TEM Imaging

A solution (10 μg/ml) in which each sample prepared according to the preparation examples was dispersed was adsorbed onto a 300-mesh Lacey carbon-coated copper grid (Ted Pella, Inc.) for 30 minutes. Prior to imaging, the grid was washed with several drops of distilled water and completely dried in a desiccator. The samples prepared as described above were analyzed using a high resolution-transmission electron microscope (HR-TEM, JEM-3010, JEOL Ltd.), and images were collected using a Gatan digital camera coupled with a microscope (MSC-794).

Experimental Example 2

Raman Spectroscopy

For measurement of Raman spectra, a powder-type product prepared according to the preparation examples was prepared on a $SiO_2$ base. Spectra were measured with a Renishaw micro-Raman spectrometer equipped with a 514.5 nm Ar excitation laser.

Experimental Example 3

FT-IR Spectroscopy

Prior to the measurement of Fourier-transform infrared (FT-IR) spectra, the powder-type samples were completely dried in a desiccator to exclude unwanted oxygen containing peaks. Spectra were measured by a typical KBR pellet method (Nicolet 6700, Thermo Scientific).

Experimental Example 4

Experimental Animals

All animal experiments were conducted according to the guidelines approved by the Institutional Animal Care and Use Committee of Seoul National University (IACUC No. SNU-170523-4). Six-week-old male C57BL/6 mice (OrientBio Inc., Sungnam, Republic of Korea) were grouped randomly, and provided 3% DSS in drinking water for 7 days (16 per group). On day 1, that is, the first day after DSS induction, mice were administered intraperitoneally 15 g/kg of nano-GOs and GQDs prepared according to the preparation examples. Body weights of the mice were measured daily, and the disease activity index (DAI) composed of body weight loss, activity, stool consistency, bleeding and a hair condition were evaluated on day 7 and day 10. After sacrificing the mice, for additional ex vivo examinations, spleen, large intestine and blood samples were collected.

Experimental Example 5

Histopathological Evaluation

Collected colon samples were fixed in 10% formalin according to typical methods including dehydration with ethanol, clearing with xylene and wax infiltration with paraffin. Paraffin-embedded blocks were sectioned to a thickness of 5 μm and stained with H&E or Masson's trichrome. The loss of goblet cells, hyperemia/edema, immune cell infiltration, the presence of crypt abscesses and epithelium loss were recorded as a histopathological index, by H&E staining. The fibrotic tissue area was measured by Masson's trichrome, and quantified using ImageJ software (version 1.46r, US National Institute of Health, Bethesda, Md., USA).

Experimental Example 6

Cytokine Production

To determine the secretion level of various cytokines, serum isolated from blood, the lysate of a colon and a culture supernatant of cells were prepared. To measure the extent of inflammation in vivo, a Cytometric Bead Array (CBA) kit (BD Bioscience, San Jose, Calif., USA) for mouse inflammation and ELISA kits for MPO and TGF-β1 (R&D Systems, Minneapolis, Minn., USA and Thermo Fisher Scientific, San Jose, Calif., USA, respectively) were used according to the manufacturers' protocols. To evaluate the secretion of cytokines induced from immune cells in vitro, CB kits for Th1/Th2/Th17 (BD Bioscience, San Jose, Calif., USA) and an ELISA kit for TGF-β1 (Thermo Fisher Scientific, San Jose, Calif., USA) were used. Results were detected using flow cytometry and spectrophotometry.

Experimental Example 7

Isolation and Culture of hMNCs

All experimental procedures related to human umbilical cord blood (hUCB) or UCB-derived cells were conducted under approval of the Boramae Hospital Institutional Review Board (IRB) and the Seoul National University IRB. Human umbilical cord blood-mononuclear cells (hUCB-MNCs) were isolated and cultured by a known method. Specifically, UCB samples were collected immediately after birth under informed consent and parent approval. The collected UCB samples were incubated after being mixed with a HetaSep solution (Stem Cell Technologies, Vancouver, Canada) in 5:1 at room temperature for 1 hour. Afterward, the supernatant was collected with Ficoll, and mononuclear cells were isolated by centrifugation at 2,500 rpm for 20 minutes. The isolated cells were washed twice with PBS. The cells isolated as described above were subjected to experiments additionally performed in subsequent in vitro analysis.

Experimental Example 8

T Cell Isolation and Polarization

Naive CD4$^+$ T cells were isolated from freshly isolated hUCB-MNCs using a human naive CD4$^+$ T cell isolation kit II (Miltenyi Biotec, Bergisch Gladbach, Germany) according to the manufacturer's instruction. The isolated CD4$^+$ T cells were cultured in RPMI1640 (Gibco BRL, Grand Island, N.Y., USA) containing 10% fetal bovine serum (FBS), an anti-CD3/28 bead activator and 20 ng/ml of IL-2, which were required for proliferation of T cell subsets. For differentiation into T cell subsets, the cells were cultured in a humidified 5% $CO_2$ atmosphere at 37° C. for 5 days in the presence/absence of nano-GOs or GQDs by adding type-specific cytokines (20 ng/ml of IFN-γ and 20 ng/ml of IL-12 for type 1 helper T cells, and 20 ng/ml of TGF-β1 for Treg cells) to a growth medium. Polarized Th1 and Treg cells were confirmed by type-specific staining and flow cytometry. For the Th1 cells, the surface was stained with CD4 antibodies, and then intracellular staining was performed with IFNγ. For Treg analysis, CD4, CD25 and IL-4 antibodies were used.

Experimental Example 9

Macrophage Isolation and Polarization

Macrophages were isolated and cultured by known methods. Specifically, macrophages were isolated from freshly-isolated hUCB-MNCs using a human CD4$^+$ T cell isolation kit (Miltenyi Biotec, Bergisch Gladbach, Germany) according to the manufacturer's instruction. The isolated CD14$^+$ cells were cultured in 10% FBS-containing RPMI1640. To polarize the cells to macrophage subtypes, the cells were cultured in a humidified 5% $CO_2$ atmosphere at 37° C. for 5 days in the presence/absence of nano-GOs or GQDs by adding type-specific cytokines (20 ng/ml of IFN-γ and 1 μg/ml of LPS of M1 cells, and 20 ng/ml of IL-4 and 20 ng/ml of IL-13 for M2 cells) to a growth medium. To confirm the polarized macrophages, type-specific staining and flow cytometry were used. As a pan-macrophage marker, CD14 antibodies were used, and as specific markers for M1 and M2 subtypes, CD86 and CD206 were applied.

Experimental Example 10

Cell Proliferation Assay

To measure cell proliferation, a cell proliferation ELISA kit (Roche, Indianapolis, Ind., USA) and a CCK-8 kit (Dojindo, Kumamoto, Japan) were used according to the manufacturers' instructions. For bromodeoxyuridine (BrdU) cell proliferation assay, a known method was used. Specifically, cells were incubated in a humidified 5% $CO_2$ atmosphere at 37° C. for 2 hours with a 100 μM BrdU labeling reagent. After being fixed in a provided FixDenat solution for 30 minutes, the cells were incubated in an anti-BrdU antibody solution for 90 minutes, and in a solution of a substrate (tetramethyl-benzidine; TMB) provided at room temperature for 5 to 30 minutes. After a stop solution was poured into each well, absorbance was measured at 450 nm and 690 nm to quantify a cell proliferation level.

Experimental Example 11

Quantitative RT-PCR

Total RNA was extracted using TRIzol (Invitrogen) according to the manufacturer's instruction. The obtained RNA was used for cDNA synthesis by a Superscript First-Strand Synthesis System (Invitrogen). A relative expression level of target mRNA was measured by an ABI 7300 detection system using a SYBR Green PCR Master Mix (Applied Biosystems, Foster City, USA). At least three independent analyses were performed for each gene.

Experimental Example 12

Cell Cycle Assay

A cell cycle assay was performed according to a known protocol. Specifically, cells were fixed with ice-cold 70% ethanol at −20° C. for 30 minutes or more. The fixed cells were washed with PBS, and incubated with 400 µl of RNase A-containing PBS (7.5 µg/ml) and propidium iodide (PI; 50 µg/ml) at 37° C. for 30 minutes. The cell cycle was analyzed by flow cytometry performed on FACScalibur using Cell Quest Software (BD Bioscience, San Jose, Calif., USA).

Experimental Example 13

Apoptosis Assay

An apoptosis assay was performed by a known method. Specifically, cells were stained with 5 µl of FITC Annexin V and 5 µl of PI in Apoptosis Detection Kits (BD Bioscience, San Jose, Calif., USA). The mixture was gently stirred by vortexing, and incubated in a room temperature dark chamber for 15 minutes. Subsequently, 400 µl of a 1×binding buffer was added to the mixture, and all samples were analyzed by flow cytometry performed on FACScalibur using Cell Quest Software.

Experimental Example 14

Immunofluorescence Assay

Cells were fixed in a 4% paraformaldehyde (PFA) PBS solution at room temperature for 15 minutes, and treated with 0.25% Triton X-100 (Sigma) for 10 minutes to increase permeability. The fixed cells were incubated with a blocking solution (5% normal goat serum) for 1 hour at room temperature, and incubated with primary antibodies at 4° C. overnight. Afterward, the cells were incubated with secondary antibodies labeled with Alexa Fluor 594 (Invitrogen), and nuclei were stained by DAPI (Sigma) staining for 5 minutes.

For whole tissue immunofluorescence, a paraffin slide was deparaffinized, and blocked with 5% normal goat serum-containing PBS. Sections were incubated with primary antibodies overnight, and then incubated with Alexa Fluor 594, followed by DAPI staining. Images were collected using a confocal microscope (Eclipse TE200, Nikon, Japan).

Experimental Example 15

Western Blotting

A colon sample was degraded with Pro-Prep (Intron Biotechnology Co., Sungnam, Republic of Korea) to extract a protein from the tissue. The obtained protein sample was separated by 10% sodium dodecyl sulfate polyacrylamide gel electrophoresis (SDS-PAGE) and transferred to a nitrocellulose membrane. After the reaction was blocked with a 3% Bovine Serum Albumin (BSA) solution, the protein on the membrane was incubated with IL-10 primary antibodies at 4° C. for at least 12 hours, and then incubated with secondary antibodies. The protein-antibody complex was detected using ECL Western blotting detection reagents and an analysis system.

Experimental Example 16

Statistical Analysis

The mean values of all results were expressed as the mean±standard error of mean (SEM). Statistical analyses were conducted using Student's 2-tailed t-test or one-way ANOVA followed by a Bonferroni post-hoc test for multi group comparisons using GraphPad Prism version 5.0 (GraphPad Software, San Diego, Calif., USA). Statistical significance was indicated in the description of the drawings.

Example 1

Characterization of Nano-GOs and GQDs

Figure 2:
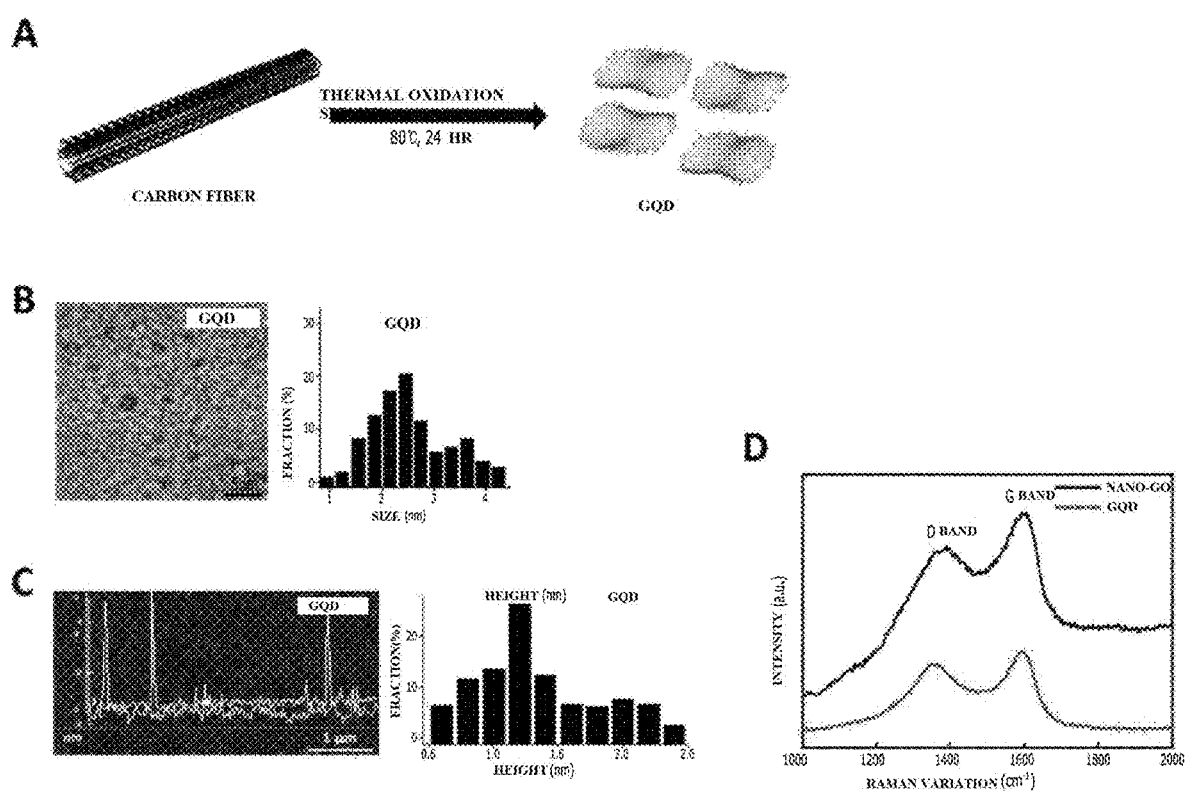
FIG. 2 shows a synthetic method and characteristics of GQDs. (A) schematically shows the synthetic method of GQDs according to the present invention. (B) shows a representative TEM image of GQDs according to the present invention and particle size distribution calculated therefrom. (C) is a representative AFM image and a line profile analysis result of GQDs according to the present invention. (D) shows representative Raman spectra of GQDs according to the present invention.

Synthetic methods for nano-GOs and GQDs used in the present invention are schematically shown in FIGS. 1A and 2A, respectively. To identify the sizes and morphologies of nano-GOs and GQDs, particles were analyzed using TEM images and selected area electron diffraction (SAED) pattern analysis (FIGS. 1B and 1C, and FIGS. 2B and 2C, respectively). The characteristics of the synthesized nano-GOs and GQDs were evaluated by atomic force microscopy (AFM) (FIGS. 1C and 2C, respectively). In addition, Raman spectra of the nano-GOs and GQDs were measured (FIGS. 1D and 2D, respectively). To place nano-GOs and GQDs in immune cells, biotinylated nano-GOs and GQDs were prepared. After modification of nano-GOs and GQDs with biotin, FT-IR spectra indicated the vibration peak of the amine.

Example 2

Figure 3:
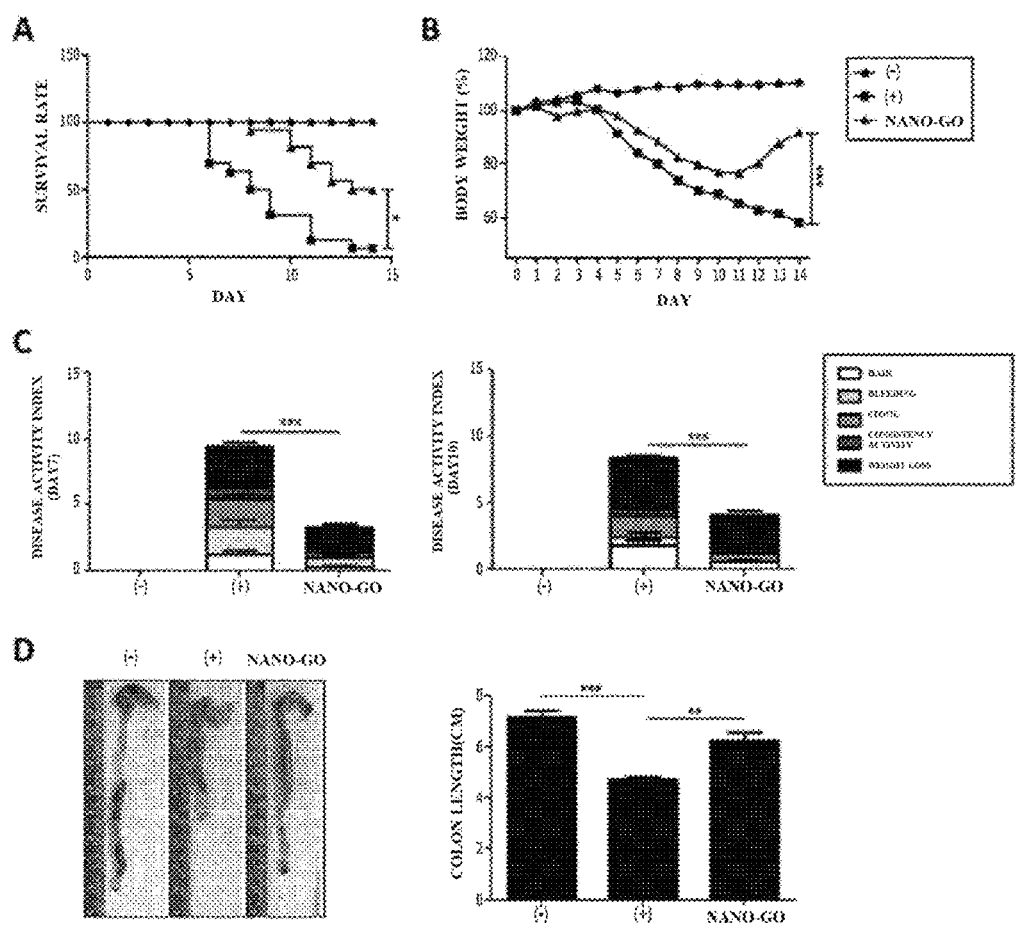
FIG. 3 shows a protective effect in DSS-induced colitis mice by intraperitoneal injection of nano-GOs. (A to D) shows an experimental result for colitis-induced mice by administering 3% DSS-containing drinking water to the mice for 7 days. On the first day after DSS administration, nano-GOs were administered intraperitoneally (300 μg/head). For clinical evaluation, the disease activity index (DAI) for (A) a survival rate, (B) a body weight loss rate and (C) colitis severity was monitored. (D) shows the morphology and length of a colon extracted from a mouse sacrificed 10 days after induction of colitis with DSS, to determine intestinal damage. n=17 to 20 mice/group. *P<0.05, P<0.01, and P<0.001. Results are expressed as the mean±SEM.
Figure 4:
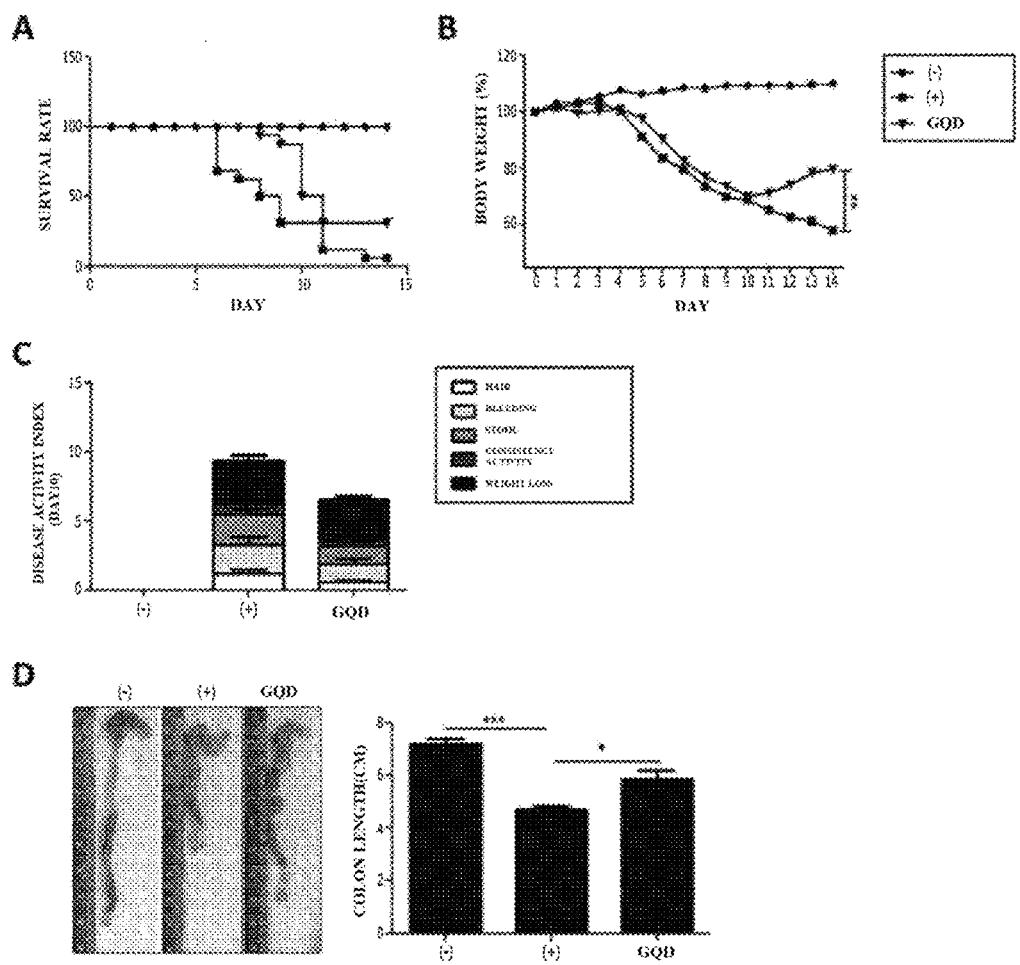
FIG. 4 shows a protective effect in DSS-induced colitis mice by intraperitoneal injection of GQDs. (A to D) shows an experimental result for colitis-induced mice by administering 3% DSS-containing drinking water to the mice for 7 days. On the first day after DSS administration, GQDs were administered intraperitoneally (300 μg/head). For clinical evaluation, the disease activity index (DAI) for (A) a survival rate, (B) a body weight loss rate and (C) colitis severity was monitored. (D) shows the morphology and length of a colon extracted from a mouse sacrificed 10 days after induction of colitis with DSS, to determine intestinal damage. n=17 to 20 mice/group. *P<0.05, P<0.01, and P<0.001. Results are expressed as the mean±SEM.
Figure 5:
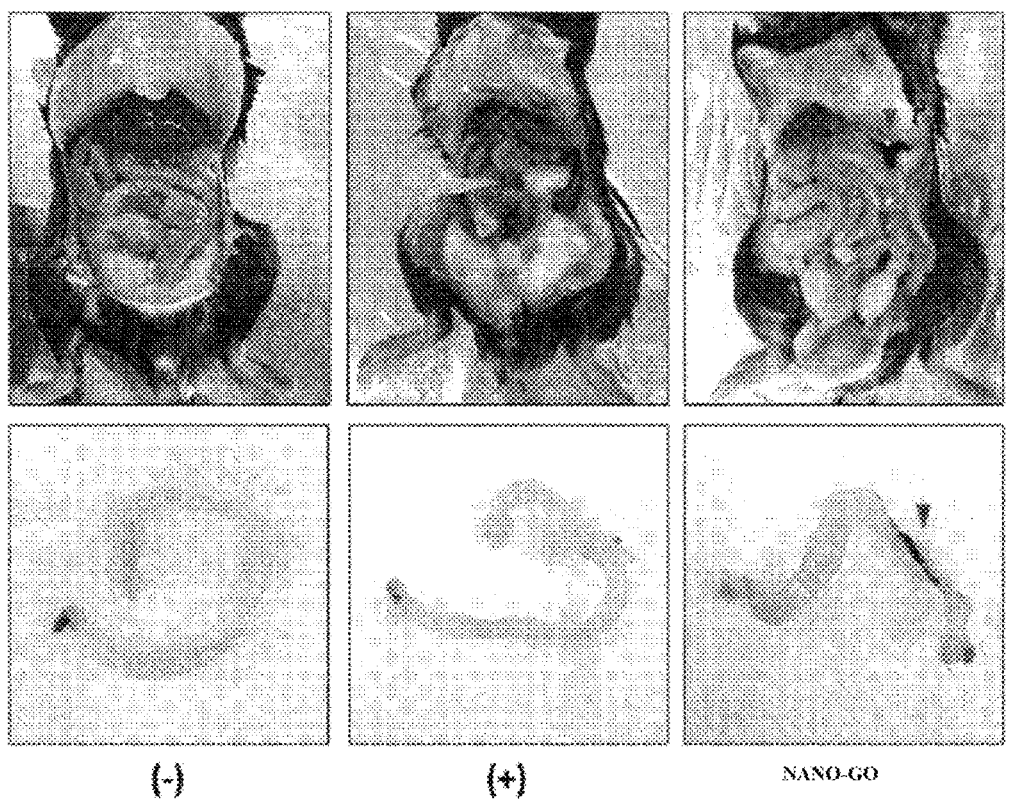
FIG. 5 shows the accumulation of nano-GOs in the abdominal cavity. On day 14 after colitis induction with DSS and the administration of nano-GOs, the mice were sacrificed. The nano-GOs were observed near the spleen and colon.
Figure 6:
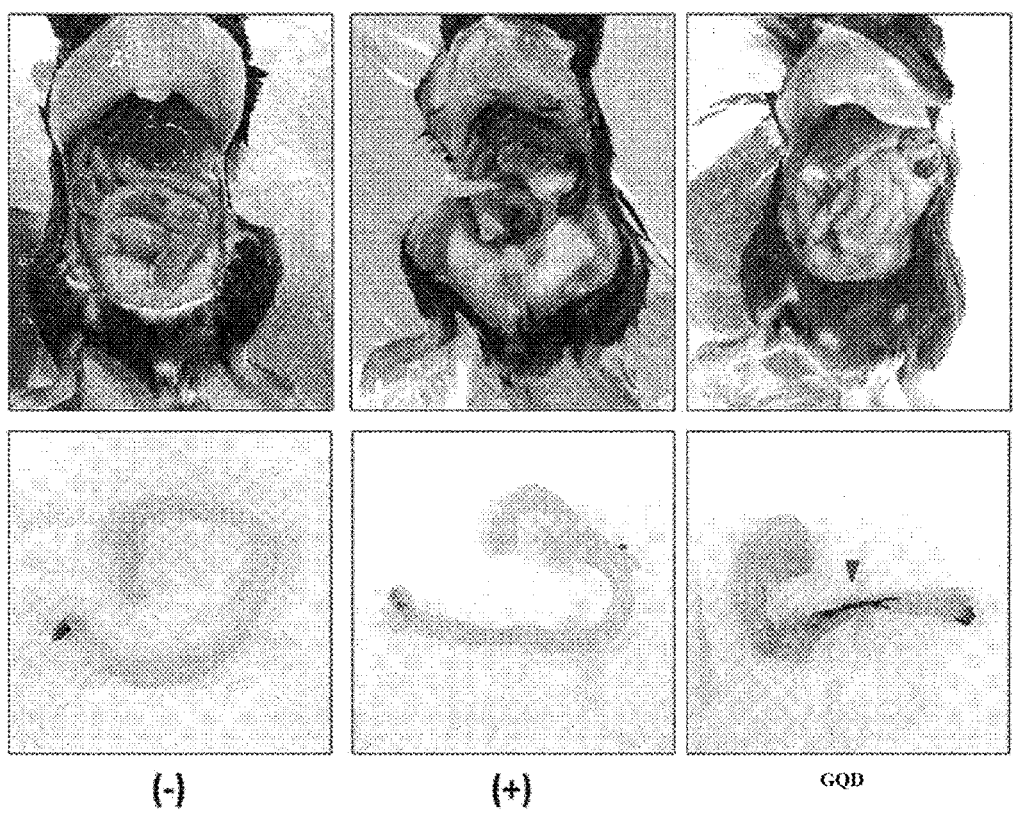
FIG. 6 shows the accumulation of GQDs in the abdominal cavity. On day 14 after colitis induction with DSS and the administration of GQDs, the mice were sacrificed. The GQDs were observed near the spleen and colon.

DSS-Induced Colitis Improvement Effect of Graphene Nano-Structure in Mouse Models To confirm a therapeutic effect of a graphene nano-structure in DSS-induced colitis mice, on day 1 after induction of colitis, each of the nano-GOs and GQDs were intraperitoneally injected into a mouse, and a body weight, a survival rate and activity were monitored for 2 weeks. As a result, both of the nano-GOs and GQDs showed an effect of protecting a mouse from severe colitis, determined by an increased survival rate and a decreased body weight (FIGS. 3A and 3B and 4A and 4B). Further, on days 7 and 10, a disease activity index was measured to confirm the progression of colitis. Like the results obtained with the survival and body weight, both of the nano-GO-treated mice and GQD-treated mice showed significantly decreased disease activity indexes (FIGS. 3C and 4C). On day 14 after colitis induction, the colons were collected from each group, and their lengths were measured. The nano-GOs and GQDs significantly suppressed the shortening of a colon length induced by colitis (FIGS. 3D and 4D). The graphene nano-structure was found near visceral organs and at an adjacent omentum (FIGS. 5 and 6). Region-specific accumulation mechanisms of nano-GOs and GQDs are not known yet. Taken together, these results show that the graphene nano-structures reduce inflammation in the colon of mice.

Example 3

Figure 7:
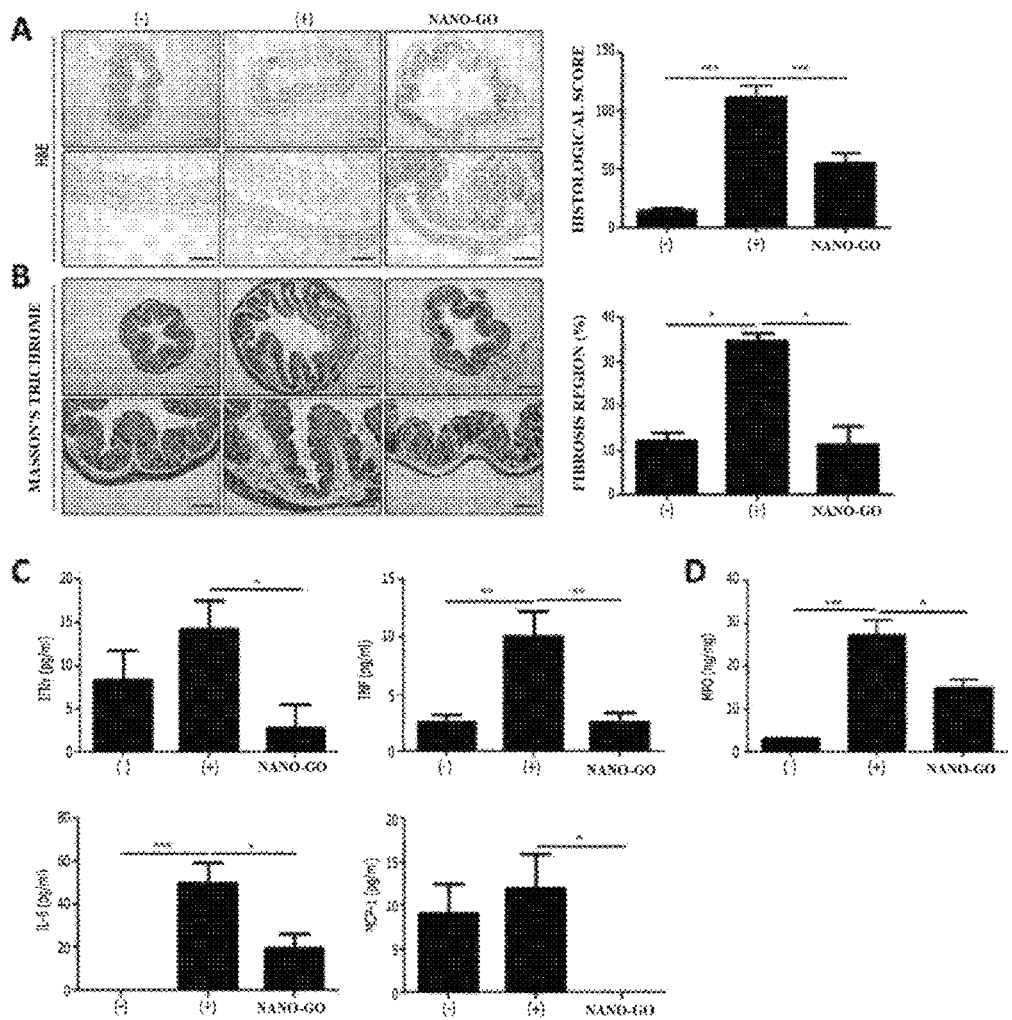
FIG. 7 shows the effects of reducing colon and systemic inflammation by nano-GOs in mice after DSS induction. Mice which have been subjected to colon cancer induction with DSS and intraperitoneal administration of nano-GOs were sacrificed on day 10 to be used for an experiment. The left panels of (A) show representative H&E-stained images of colon sections, and the right panels of (A) show results of histopathological evaluation based on lymphocyte infiltration and intestinal damage. Scale bar=1 mm (upper) and 500 μm (lower). The left panels of (B) show Masson's trichrome-stained results for colons to evaluate fibrosis, and the right panels of (B) show quantitative analysis results for fibrotic areas. Scale bar=1 mm (upper) and 500 μm (lower). Serum was collected from a colitis mouse and the secretion level of an indicated cytokine using a cytometric bead array (CBA) assay was measured and shown in (C). (D) shows myeloperoxidase (MPO) measured in colon tissue.
Figure 8:
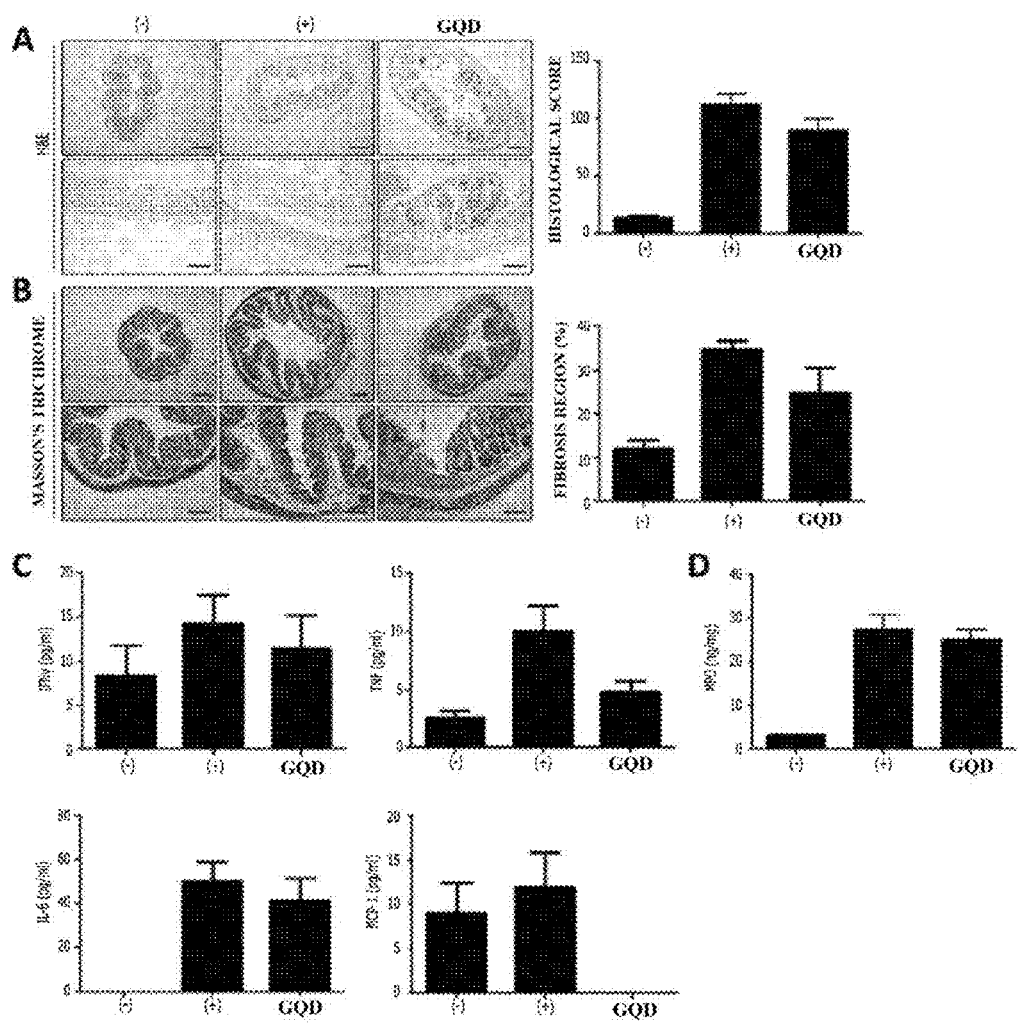
FIG. 8 shows effects of reducing colonic and systemic inflammation by GQDs in mice after DSS induction. Mice have been subjected to induction of colorectal cancer with DSS and intraperitoneal administration of GQDs, and on day 10, they are sacrificed for an experiment. The left panels of (A) show representative H&E-stained images of colon sections, and the right panels of (A) show results of histopathological evaluation based on lymphocyte infiltration and intestinal damage. Scale bar=1 mm (upper) and 500 μm (lower). The left panels of (B) show Masson's trichrome-stained results for colons to evaluate fibrosis, and the right panels of (B) show quantitative analysis results for fibrotic areas. Scale bar=1 mm (upper) and 500 μm (lower). Serum was collected from a colitis mouse and the secretion level of an indicated cytokine using CBA assay was measured and shown in (C). (D) shows MPO measured in colon tissue.
Figure 9:
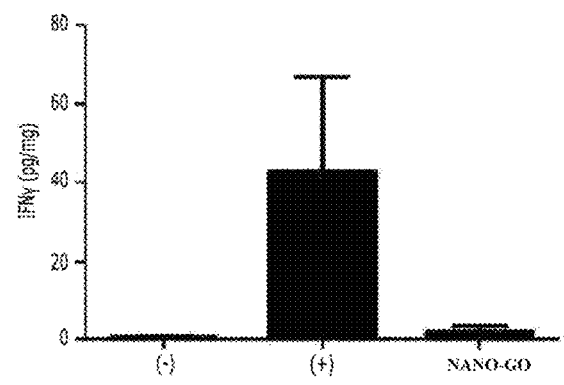
FIG. 9 shows CBA assay results for colon tissue by nano-GOs after colitis induction. The secretion level of an indicated cytokine in colon tissue was measured by CBA assay.
Figure 9:
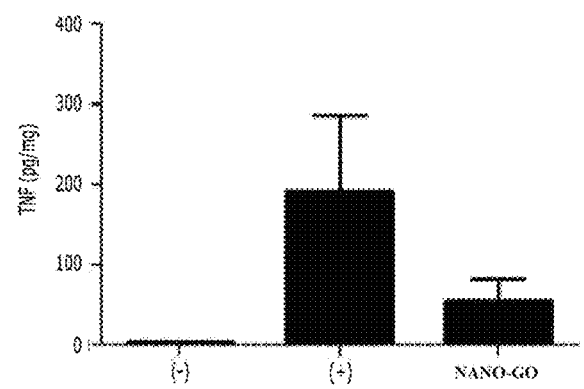
Figure 9:
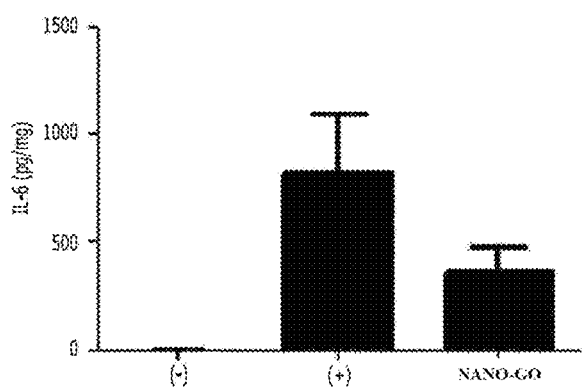
Figure 9:
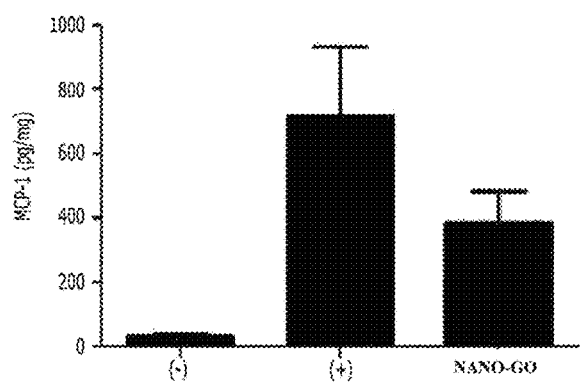

Impairment of DSS-Induced Colitis Inflammatory Response by Graphene Nano-Structure The histological analysis of the colon showed that DSS induces epithelium destruction, submucosal edema, crypt abscesses and lymphocytic infiltration (FIGS. 7A and 8A). In nano-GO-treated mice and GQD-treated mice, inflammatory lesions were rarely found or reduced, compared with a PBS-treated mouse. Further, to evaluate mucosal and submucosal fibroses of the colon, which were induced by colitis, Masson's trichrome straining was performed. The PBS-treated mouse showed collagen deposition detected by blue staining. Nano-GOs and GQDs also reduced collagen accumulation. GQD injection prevented colon shortening. To evaluate systemic inflammation, the level of proinflammatory cytokines secreted from serum was measured using CBA assay. The induction of IFNγ, which is the major cytokine accounting for most of Crohn's disease, was suppressed in the nano-GO-treated mice and the GQD-treated mice (FIGS. 7C and 8C). In addition, the treatment of nano-GOs and GQDs reduced downstream cytokines of IFN-γ, TNF, IL-6 and MCP-1. Myeloperoxidase (MPO), which is a neutrophil granule constituent, is known to be proportional to the number of migrated neutrophils. The nano-GO-treated mice and GQD-treated mice showed lower MPO activity than the PBS-treated mouse in the colon tissue, indicating that the graphene nano-structure inhibits the migration of neutrophils and inflammation (FIGS. 7D and 8D). Therefore, this result shows that the graphene nano-structures have an immunosuppressive effect in the Crohn's disease models.

Example 4

Inhibitory Effect of Graphene Nano-Structure on $CD4^+$ T Cell Activity

Figure 10:
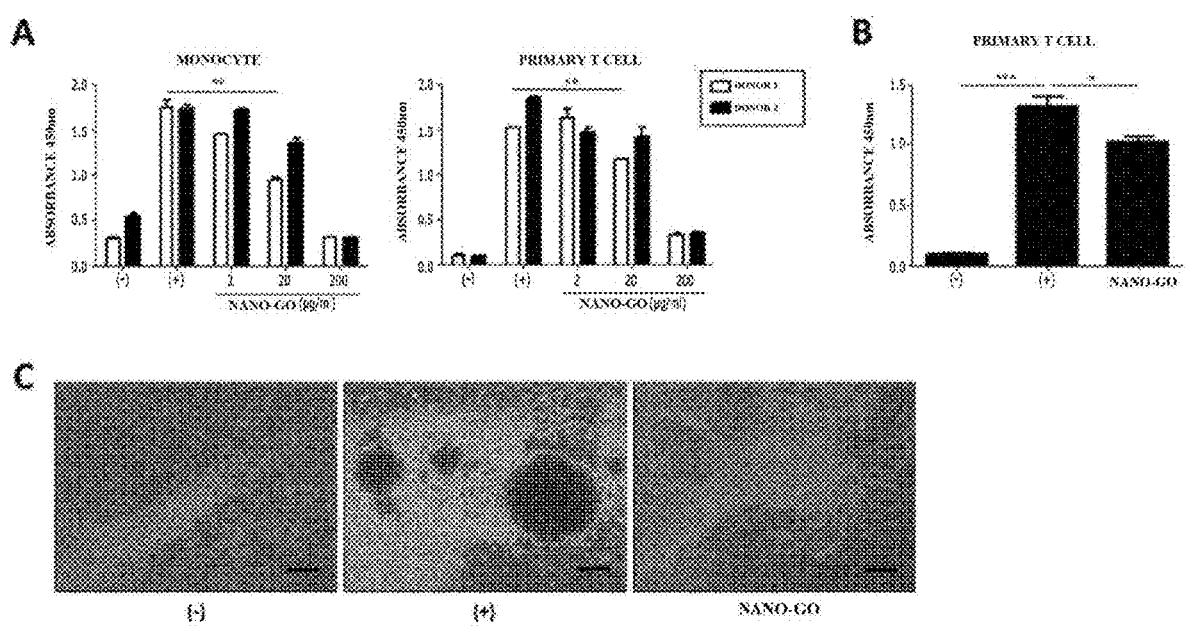
FIG. 10 shows experimental results to determine the optimal in vitro concentration of nano-GOs. The left graph of (A) shows mononuclear cells (MNCs) activated by concanavalin A in the presence of nano-GOs at an indicated concentration after being isolated from human umbilical cord blood (hUCB), and the right graph of (A) shows CD4+ T cells purified from hUCB and cultured in the presence of nano-GOs at an indicated concentration. (B and C) are results obtained by adding 20 μg/ml of GOs to Th1 cells for 2 days, wherein (B) shows proliferation measured by a BrdU assay, and (C) shows a set of representative images of Th1 cells from respective groups.
Figure 11:
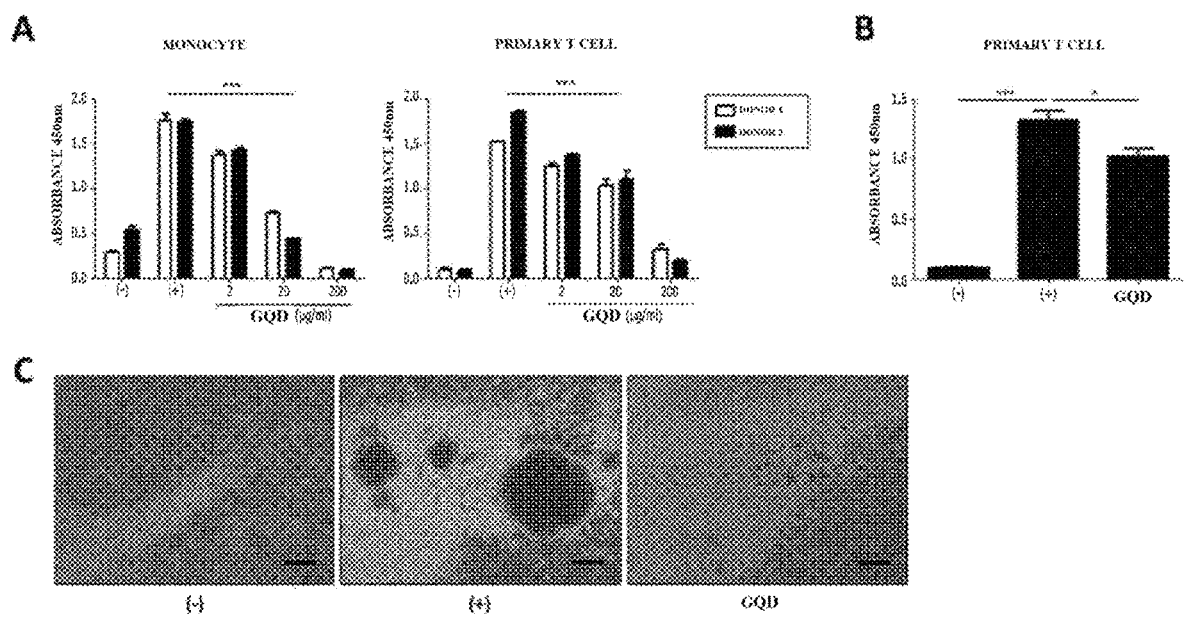
FIG. 11 shows experimental results to determine an optical in vitro concentration of GQDs. The left graph of (A) shows MNCs activated by concanavalin A in the presence of GQDs at an indicated concentration after being isolated from human umbilical cord blood (hUCB), and the right graph of (A) shows CD4+ T cells purified from hUCB and cultured in the presence of GQDs at an indicated concentration. (B and C) are results obtained by adding 20 μg/ml of GQDs to Th1 cells for 2 days, wherein (B) shows proliferation measured by a BrdU assay, and (C) shows a set of representative images of Th1 cells from respective groups.
Figure 12:
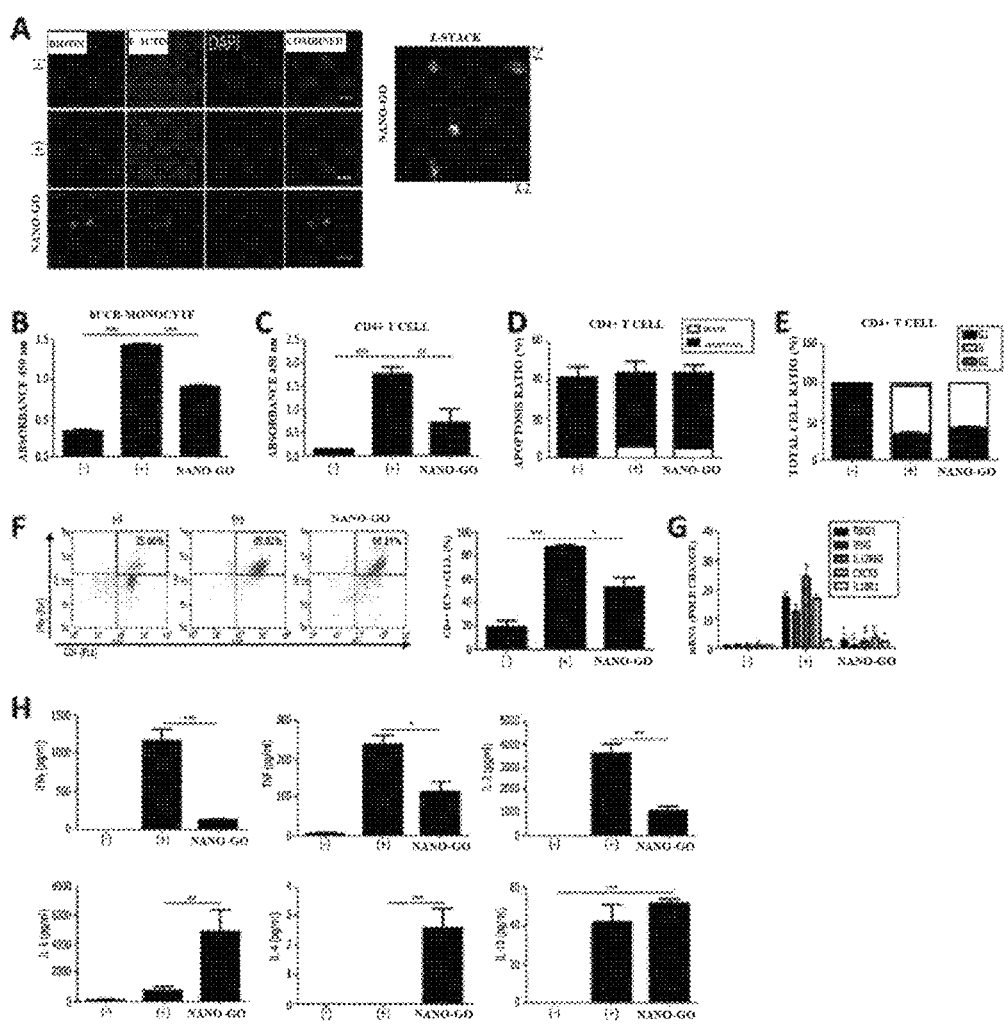
FIG. 12 shows an inhibitory effect of nano-GOs on the activity of Th1-differentiated cells. CD4+ T cells are isolated from hUCB, and induce differentiation into Th1 cells using anti-CD3 and CD28 beads in combination with IL-12 and IFN-γ in the presence of nano-GOs. (A) shows localization in Th1-differentiated cells by treatment of biotin-labeled nano-GOs. To detect biotin-labeled nano-GOs, anti-GFP-biotin was used. The right panel shows a Z-stack image of Th1 cells treated with nano-GOs. Scale bar=10 μm. (B) shows MNCs isolated from hUCB and stimulated by concanavalin A along with nano-GOs. MNCs were cultured for 2 days and measured by a BrdU assay. (C) is a result of evaluating the proliferation of Th1 cells cultured for 2 days in the presence of nano-GOs by a BrdU assay. (D) is a result of analyzing apoptosis of Th1 cells using an Annexin V apoptosis detection kit. (E) is a result of a cell cycle assay performed on Th1 cells using propidium iodide (P.I.) staining. (F) is a result of analyzing the percentage of IFN-γ-expressing CD4+ T cells by flow cytometry. (G) is a result of confirming mRNA expression of Th1 cells per group for an indicated Th1-specific marker. (H) is a result of analyzing an indicated Th1-specific cytokine in a Th1 cell supernatant by CBA assay.
Figure 13:
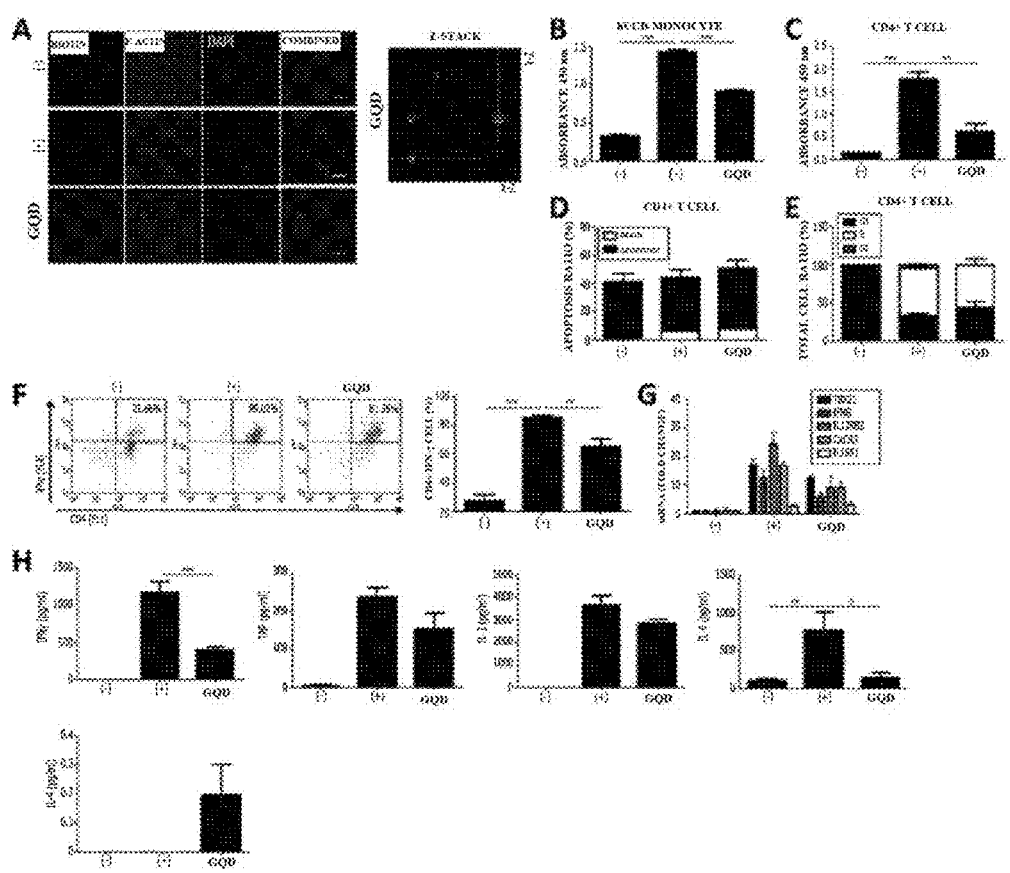
FIG. 13 shows an inhibitory effect of GQDs on the activity of Th1-differentiated cells. CD4+ T cells are isolated from hUCB, and induce differentiation into Th1 cells using anti-CD3 and CD28 beads in combination with IL-12 and IFN-γ in the presence of GQDs. (A) shows localization in Th1-differentiated cells by treatment with biotin-labeled GQDs. To detect the biotin-labeled GQDs, anti-GFP-biotin was used. The right panel shows a Z-stack image of Th1 cells treated with GQDs. Scale bar=10 μm. (B) shows MNCs isolated from hUCB and stimulated by concanavalin A along with GQDs. MNCs were cultured for 2 days and measured by a BrdU assay. (C) is a result of evaluating the proliferation of Th1 cells cultured for 2 days in the presence of GQDs by a BrdU assay. (D) is a result of analyzing apoptosis of Th1 cells using an Annexin V apoptosis detection kit. (E) is a result of a cell cycle assay performed in Th1 cells using propidium iodide (P.I.) staining. (F) is a result of analyzing the percentage of IFN-γ-expressing CD4+ T cells by flow cytometry. (G) is a result of confirming mRNA expression of Th1 cells per group for an indicated Th1-specific marker. (H) is a result of analyzing an indicated Th1-specific cytokine in a Th1 cell supernatant by CBA assay.

In consideration that Th1 cells play a critical role in enterocolitis, a direct effect of a graphene nano-structure in $CD4^+$ T cells was examined. First, to determine an appropriate concentration, MNCs and primary $CD4^+$ T cells were treated with nano-GOs and GQDs at various concentrations (FIGS. 10A and 11A). 20 μg/ml each of nano-GOs and GQDs effectively inhibited the proliferation of MNCs and T cells without toxicity, respectively (FIGS. 10B and 10C and FIGS. 11B and 11C, respectively). To place the graphene nano-structure in the $CD4^+$ T cells, the cells were treated with biotin-labeled nano-GOs or GQDs using GFP-biotin antibodies, and $CD4^+$ Th1 cells were immunostained (FIGS. 12A and 13A). The biotin-labeled nano-GOs and GQDs were detected in the T cells. This shows that the materials can be internalized into cells. To examine an effect of the graphene nano-structure on the proliferation of immune cells, hUCB-derived MNCs and $CD4^+$ T cells were cultured after treatment with nano-GOs or GQDs (FIGS. 12B and 12C and FIGS. 13B and 13C, respectively). The graphene nano-structure effectively inhibited the proliferation of MNCs and $CD4^+$ T cells. The Th1 inhibitory property of the graphene nano-structure may be a main mechanism exhibiting a therapeutic effect in Crohn's disease models. Annexin V assay showed that nano-GOs and GQDs do not affect an apoptosis pathway (FIGS. 12D and 13D). However, nano-GOs and GQDs slightly increased the G1 phase in the cell cycle, indicating that the progression of the cell cycle is inhibited (FIGS. 12E and 13E). To examine a specific effect of the graphene nano-structure on Th1 cells, $CD4^+$ T cells were purified from hUCB, and differentiated into a Th1 type in the presence of nano-GOs or GQDs (FIGS. 12F and 13F). As a result, both of nano-GOs and GQDs significantly inhibited Th1 differentiation. $CD4^+$ T cells cultured under a Th1 polarized condition were subjected to analysis of Th1-specific gene expression (FIGS. 12G and 13G). The nano-GO/GQD-treated $CD4^+$ T cells showed significantly inhibited Th1 gene expression. To analyze a functional change in the nano-GO/GQD-treated Th1 cells, a concentration of cytokines secreted in a cell culture supernatant was measured (FIGS. 12H and 13H). The secretion of IFN-γ, TNF and IL-2 in the nano-GO/GQD-treated cells significantly decreased. Meanwhile, IL-6, IL-4 and IL-10 levels increased in the nano-GO/GQD-treated Th1 cells. These results show that colitis is alleviated due to the inhibition of a Th1 response and the promotion of regulatory T cell activity by the graphene nano-structures.

Example 5

Increase in in vivo Regulatory T Cell Infiltration by Graphene Nano-Structure

Figure 14:
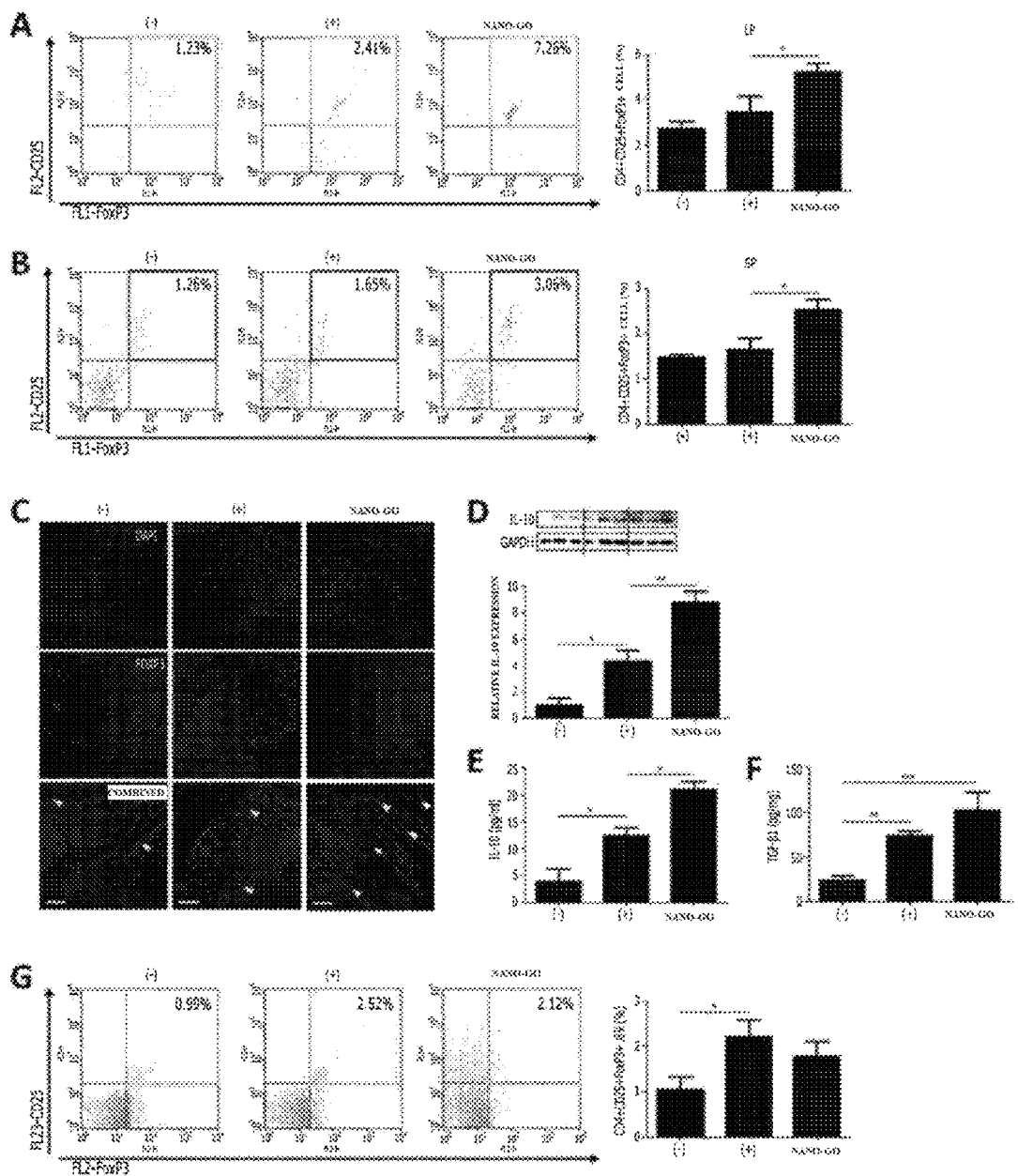
FIG. 14 shows an indirect increase in proportion of CD4+CD25+FoxP3+ regulatory T cells in vivo by nano-GOs. Colons and spleens are collected for an in vitro experiment after nano-GO-administered mice were sacrificed on day 15. The results are obtained from 5 to 6 mice per group. (A) Colon infiltration and (B) spleen infiltration of CD4+CD25+ FoxP3+ regulatory T cells were measured by flow cytometry. (C) shows regulatory T cells observed in the colon by immunostaining with FoxP3 (green), Scale bar=50 μm. FoxP3+ cells were indicated by ▼. The IL-10 expression of a colon lysate was confirmed by (D) Western blotting and (E) CBA assay. (F) shows a result of analyzing the secretion level of TGF-β1 in the colon by ELISA. (G) shows the polarization of Treg cells and a result of analyzing CD4+ CD25+FoxP3+ cells by flow cytometry. *P<0.05, P<0.01, and *P<0.001. The results are expressed as the mean±SEM.
Figure 15:
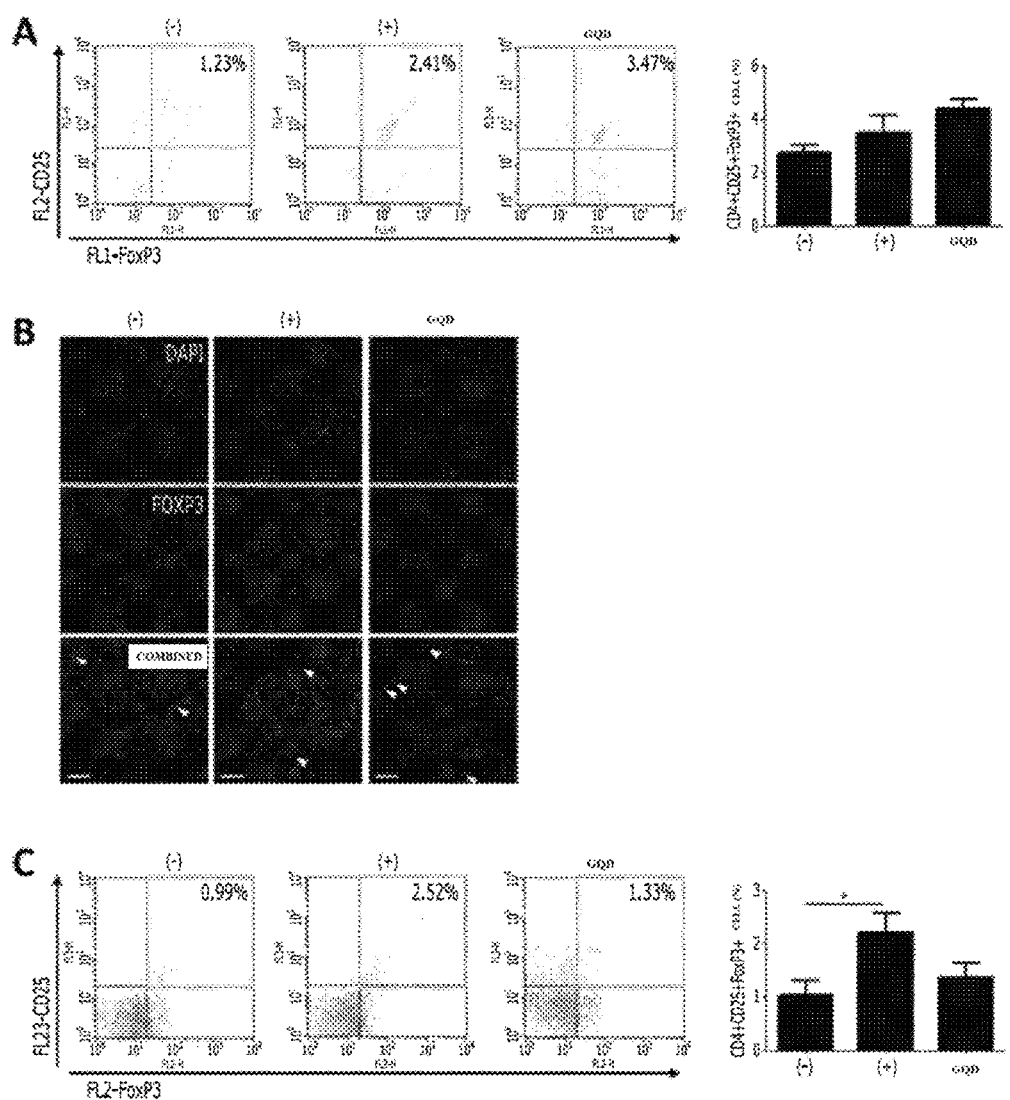
FIG. 15 shows an indirect increase in proportion of CD4+CD25+FoxP3+ regulatory T cells in vivo by GQDs. Colons and spleens are collected for an in vitro experiment after GQD-administered mice were sacrificed on day 15. The results are obtained from 5 to 6 mice per group. (A) Colon infiltration and (B) spleen infiltration of CD4+CD25+ FoxP3+ regulatory T cells were measured by flow cytometry. (C) shows regulatory T cells observed in the colon by immunostaining with FoxP3 (green), Scale bar=50 μm. FoxP3+ cells were indicated by ▼. The IL-10 expression of a colon lysate was confirmed by (D) Western blotting and (E) CBA assay. (F) shows a result of analyzing the secretion level of TGF-β1 in the colon by ELISA. (G) shows the polarization of Treg cells and a result of analyzing CD4+ CD25+FoxP3+ cells by flow cytometry. *p<0.05, P<0.01, and *P<0.001. The results are expressed as the mean±SEM.

The inventors had confirmed that recovery from experimental colitis is accompanied by expansion and infiltration of regulatory T cells through previous research. Accordingly, the inventors performed flow cytometry to examine whether the administration of a graphene nano-structure affects localization of Treg cells. Specifically, the administration of nano-GOs or GQDs increased colonic infiltration and splenic polarization of $CD4^+CD25^+FoxP3^+$ Treg cells (FIGS. 14A and 15A). By immunohistochemistry, it was confirmed that increased colonic infiltration of the Treg cells were observed in the nano-GO/GQD-treated mice (FIGS. 14 and 15). Subsequently, the expression of IL-10 and TGF-β1, which are major derivatives and products of the Treg population and play a major role in Treg-mediated colitis alleviation, was determined. The IL-10 expression significantly increased in the colon of a nano-GO-treated mouse. In addition, to examine whether the graphene nano-structure directly affects the polarization of the Treg cells, naive $CD4^+$ cells were induced to a regulatory T cell lineage in the presence of nano-GOs or GQDs. As a result, nano-GOs and GQDs did not have an effect of increasing Treg polarization, but rather interfered with the polarization.

Taken together, such results show that the graphene nano-structures increase the number of regulatory T cells and cytokines related thereto in vivo, which are not mediated by a direct effect on Treg polarization.

Example 6

Conversion of M1 Macrophages into M2 Type During Immune Response by Graphene Nano-Structure Example 6-1

Conversion of M1 Macrophages into M2 Type During Immune Response by Nano-GOs

Figure 16:
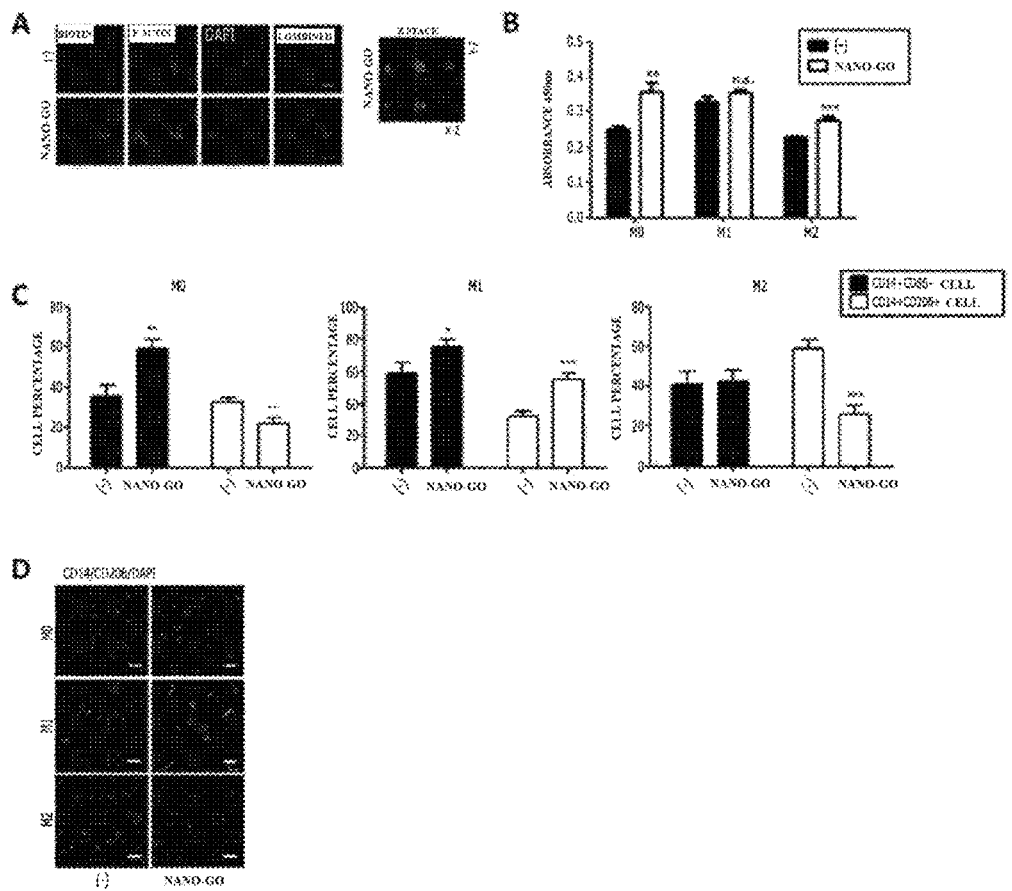
FIG. 16 shows the role of nano-GO in conversion of M1 macrophages to alternatively activated M2-type cells. CD14+ cells were isolated from hUCB and cultured in the presence of nano-GOs. (A) is a result of observing localization by treating CD14+ macrophage-like cells with biotin-labeled nano-GOs. The right panel is a Z-stack image of nano-GO-treated CD14+ cells, Scale bar=10 μm. The isolated CD14+ cells were polarized into type-specific inducer cytokines, such as M0, M1 and M2-type cells in the presence of nano-GOs. After seven days of culture, (B) confirms cell proliferation by a CCK-8 assay. A type-specific cell surface CD marker was analyzed by (C) flow cytometry and (D) immunocytochemistry. *P<0.05, P<0.01, and *P<0.001. The results are expressed as the mean±SEM.
Figure 18:
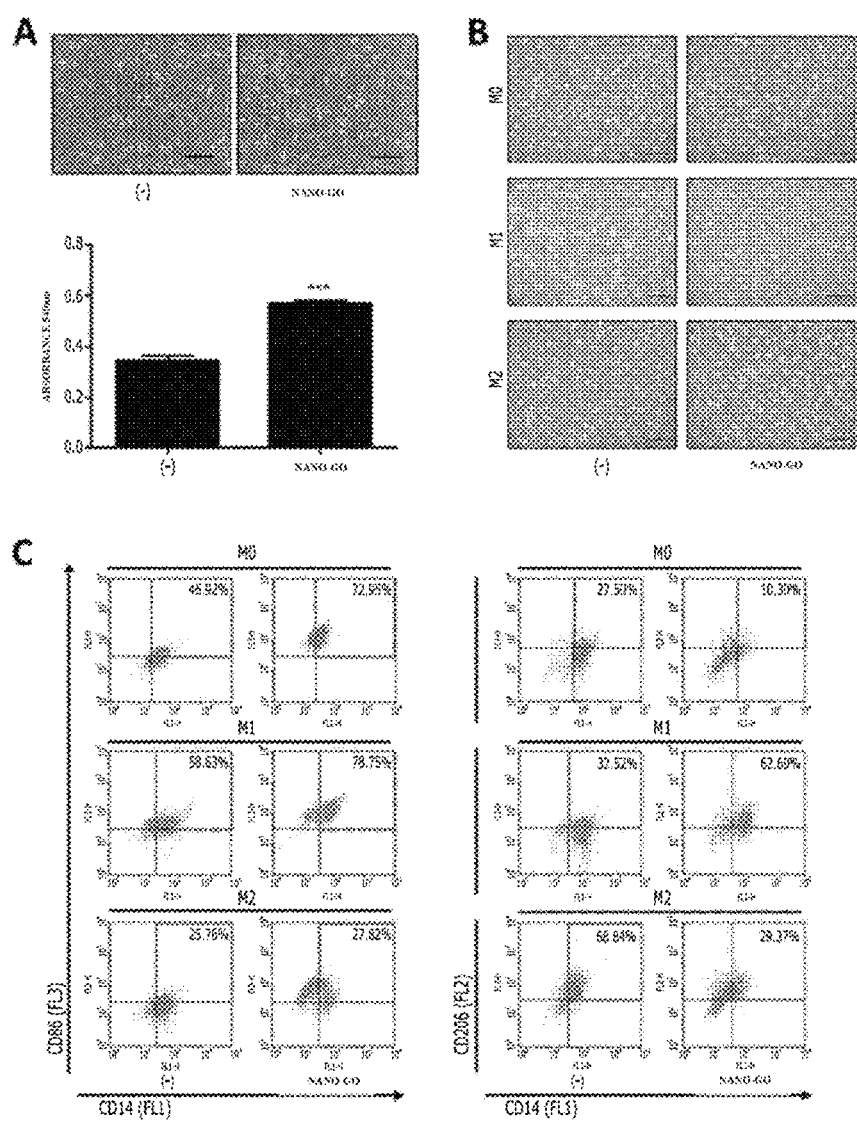
FIG. 18 shows changes in cell morphology and survival rate as well as the differentiation ability of a macrophage by nano-GOs. The upper panels of (A) show phase-contrast images of Raw 264.7 cells cultured with nano-GOs. Scale bar=100 μm. The lower panel shows the cell survival rate determined by an MTT assay. The isolated CD14+ cells were polarized into type-specific induced cytokines such as M0, M1 and M2-type cells in the presence of nano-GOs. (B) shows a phase difference image (Scale bar=200 μm), and (C) shows dot plot images according to flow cytometry. *** P<0.001. The results are expressed as the mean±SEM.

Due to an imbalance between tolerogenic and protective immune responses of intestinal macrophages, colonic inflammation may occur and may be improved by alternatively activated M2-type macrophages serving to collect Treg cells and secretory cytokines thereof. Accordingly, it was examined whether treatment of nano-GOs affects the cell fate determination of macrophages. The internalization of nanoparticles was confirmed by a biotinylated carbon nano-structure and immunohistochemistry (FIG. 16A). According to the nano-GO treatment, the proliferation of a mouse macrophage cell line, Raw 264.7 cells, increased, and an enlarged cell morphology was observed (FIG. 18A). Similar to the Raw 264.7 cells, when cultured as M0 and M2-type cells with nano-GOs, primarily isolated $CD14^+$ cells showed increased proliferation. On the other hand, nano-GOs did not make any effective change in M1-type cells (FIGS. 16B and 18B).

A cell surface marker assay was conducted using flow cytometry to confirm an effect of nano-GOs on macrophage type-specific polarization. The graphene nano-structure was likely to induce naive CD14$^+$ cells to a proinflammatory (classical) type of macrophage without other additional cytokines. With regard to M2-type macrophages, nano-GO treatment induced an increase in both of CD14$^+$CD86$^+$ cells and CD14$^+$CD206$^+$ cells. The expression of a CD206 surface marker on CD14$^+$ cells was confirmed by immunohistochemistry (FIG. 16D). Such results show that nano-GOs play a role in inflammatory resolution by downregulating the M1-like property of macrophages activated as a proinflammatory (classical) type and converting the macrophages into M2 types.

Example 6-2

Conversion of M1 Macrophage into M2 Type During Immune Response by GQDs

Figure 17:
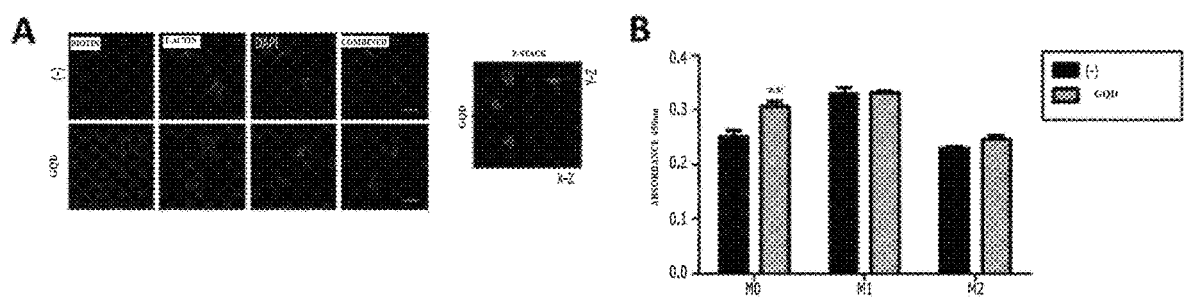
FIG. 17 shows the role of GQD in conversion of M1 macrophages to alternatively activated M2-type cells. CD14+ cells were isolated from hUCB and cultured in the presence of GQDs. (A) is a result of observing localization by treating CD14+ macrophage-like cells with biotin-labeled GQDs. The right panel is a Z-stack image of GQD-treated CD14+ cells, Scale bar=10 μm. The isolated CD14+ cells were polarized into type-specific inducer cytokines, such as M0, M1 and M2-type cells in the presence of GQDs. After seven days of culture, (B) confirms cell proliferation by a CCK-8 assay. A type-specific cell surface CD marker was analyzed by (C) flow cytometry and (D) immunocytochemistry. *P<0.05, P<0.01, and *P<0.001. The results are expressed as the mean±SEM.

Whether the treatment with GQDs affects the cell fate determination of macrophages was examined. The internalization of nanoparticles was identified by a biotinylated carbon nano-structure and immunohistochemistry (FIG. 17A). When being cultured as M0-type cells with GQDs, primarily isolated CD14$^+$ cells showed increased proliferation, but there were no significant changes in M1 and M2-type cells (FIG. 17B).

Figure 19:
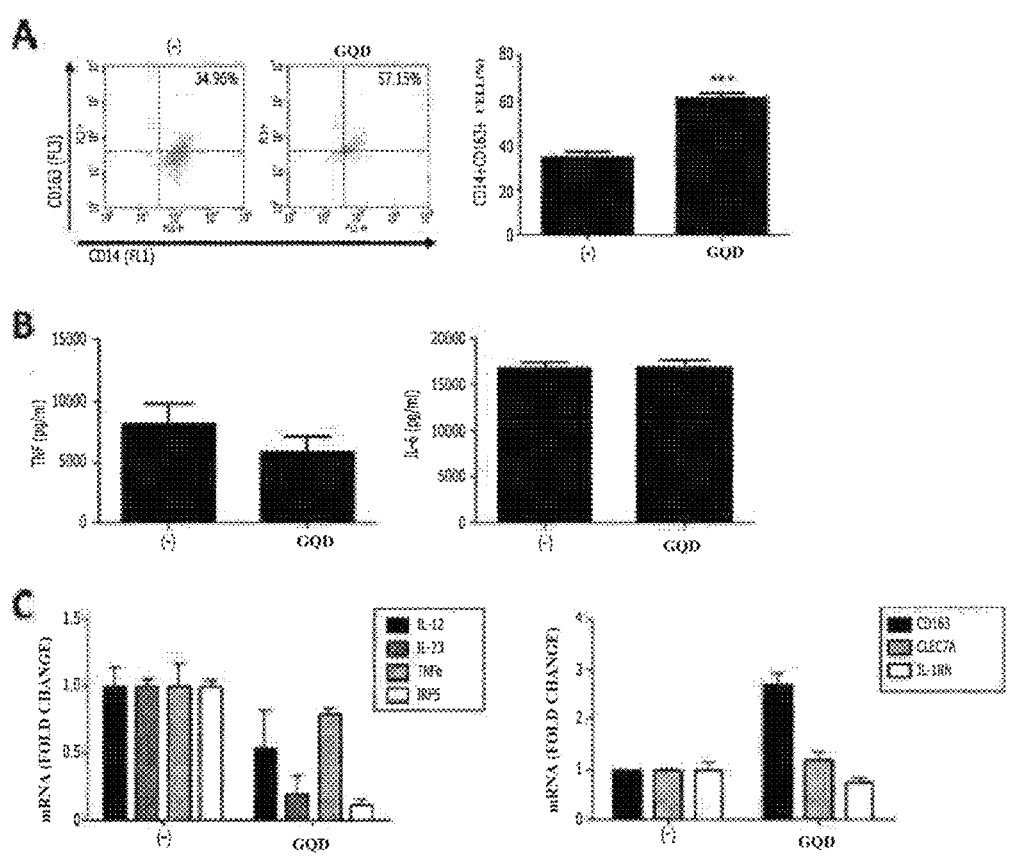
FIG. 19 shows that M2b macrophages are a main subtype among GQD-mediated M2-polarized cells. The isolated CD14+ cells were cultured with GM-CSF for 2 days, and then cultured with IFN-γ and LPS for 5 days to differentiate into M1-type macrophages. After culture for 7 days, the medium in which the cells were cultured was recovered and then analyzed. (A) shows the expression of CD163 confirmed by flow cytometry. (B) shows TNF, IFN-γ and IL-6 secretion levels measured by CBA assay. (C) shows the result of analyzing M1 and M2-type-specific gene expression by qRT-PCR.

A cell surface marker assay was conducted using flow cytometry to confirm an effect of GQDs on macrophage type-specific polarization. To confirm that the conversion of proinflammatory (classical) activated M1-type macrophages into anti-inflammatory M2 subtypes is caused by GQD treatment, additionally, the expression of another M2 type-specific property was examined. As a result, the expression of a hemoglobin scavenger receptor, CD163, increased in the presence of GQDs (FIGS. 19A and 19C). A secretion level of TNF, which is a representative proinflammatory cytokine, was slightly reduced, but there was no significant change in IL-6 level (FIG. 19B). Further, GQD treatment inhibited the mRNA expression of IL-12, IL-23, TNFα and an M1 type-specific transcription factor IRF5. Meanwhile, the GQD treatment was likely to maintain or slightly increase the expression of CLEC7A and IL-1ra (FIG. 19C).

Such results show that GQDs play a role in inflammatory resolution by downregulating an M1-like property of macrophages activated as a proinflammatory (classical) type and converting the macrophages into M2 types.

Example 7

Main Subtype M2b of Generally Activated Macrophages Induced by Nano-GOs

Figure 20:
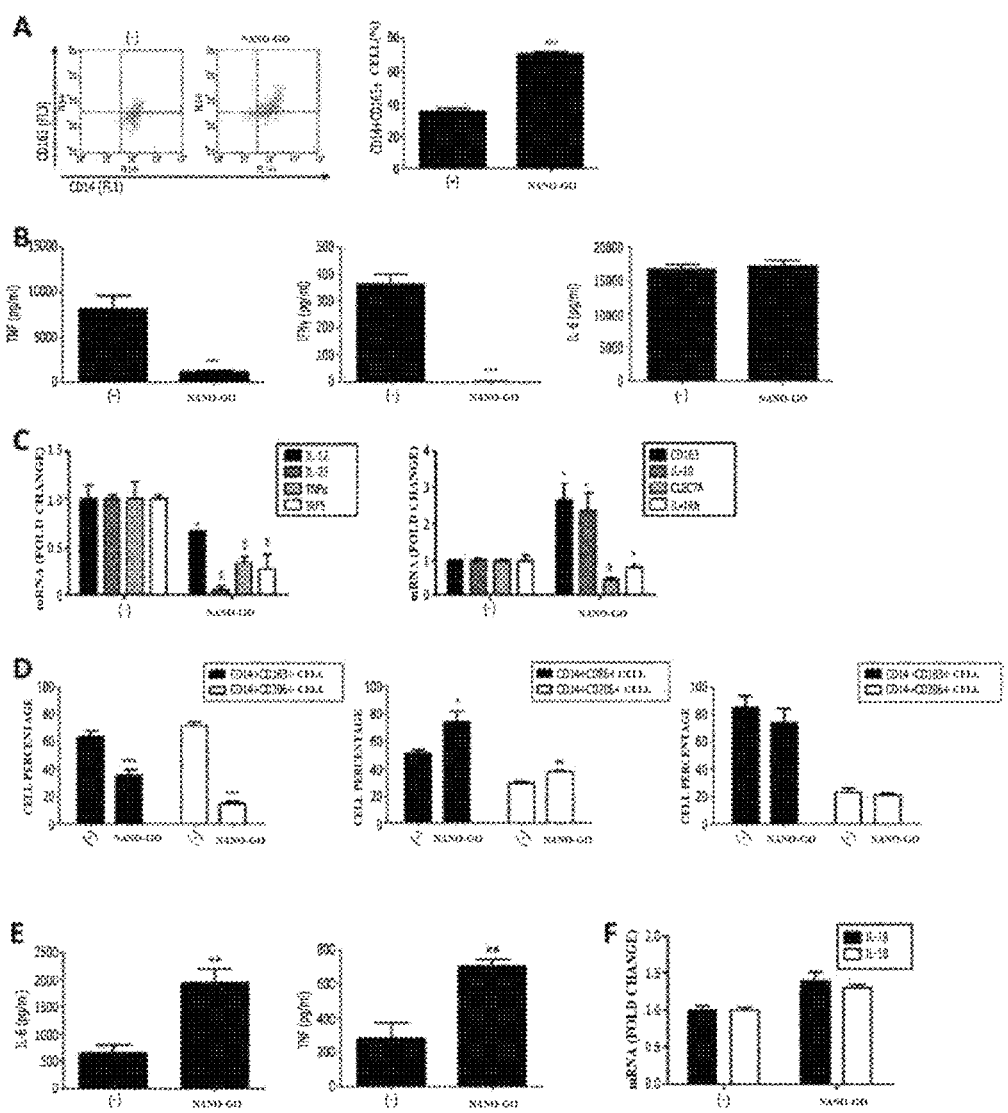
FIG. 20 shows that an M2b macrophage is a main subtype among nano-GO-mediated M2-polarized cells. The isolated CD14+ cells were cultured with GM-CSF for 2 days, and then cultured with IFN-γ and LPS for 5 days to differentiate into M1-type macrophages. After culture for 7 days, the medium in which the cells were cultured was recovered and then analyzed. (A) shows the expression of CD163 confirmed by flow cytometry. (B) shows TNF, IFN-γ and IL-6 secretion levels measured by CBA assay. (C) shows the result of analyzing M1 and M2-type-specific gene expression by qRT-PCR. For M2 subtype polarization, $CD14^+$ cells were cultured with M-CSF for 2 days, and then cultured with specific cytokine combinations (M2a, IL-4 and IL-13; M2b, Poly I:C, IL-1β and LPS; and M2c, IL-10 and TGF-β1) for 5 days. (D) shows results of detecting the expression of a M2 subtype-specific CD marker by flow cytometry. (E) shows TNF and IL-6 secretion levels measured by CBA assay. (F) shows a result of confirming the gene expression of IL-1β and IL-10 by qRT-PCR. *$P<0.05$, $P<0.005$, and *$P<0.001$. The results are expressed as the mean±SEM.

To confirm that classically activated M1-type macrophages are converted into anti-inflammatory M2 subtypes by nano-GO treatment, additionally, the expression of another M2 type-specific property was examined. The expression of a hemoglobin scavenger receptor, CD163, increased in the presence of nano-GOs (FIGS. 20A and 20C). Secretion levels of TNF and IFN-γ, which are representative proinflammatory cytokines, were significantly reduced, but there was no significant change in IL-6 level (FIG. 20B). Further, nano-GO treatment inhibited the mRNA expression of IL-12, IL-23, TNFα and an M1 type-specific transcription factor IRF5. On the other hand, a level of the most important marker IL-10 of the M2 macrophages increased. However, the nano-GO treatment did not improve the expression of CLEC7A and IL-1ra, but rather inhibited it (FIG. 20C).

Figure 21:
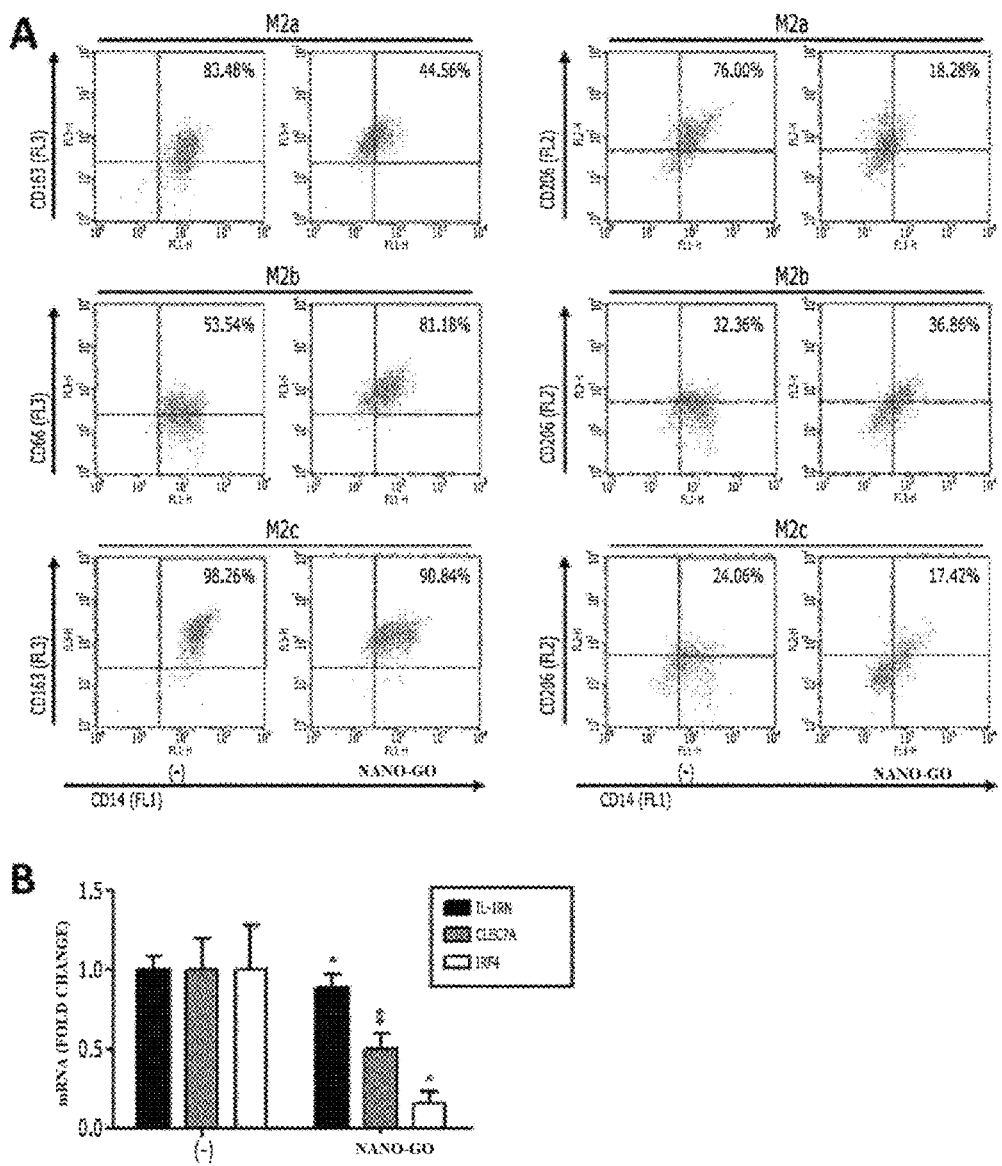
FIG. 21 shows responses of M2-subtype macrophages by treatment with nano-GOs. $CD14^+$ cells were cultured with M-CSF for 2 days, and then cultured with a specific cytokine combination for 5 days. (A) shows dot plot images according to flow cytometry. (B) is a result of M2a subtype-specific gene expression by qRT-PCR. *$P<0.05$, $P<0.005$, and *$P<0.001$. The results are expressed as the mean±SEM.

The M2 macrophages may be classified into three or more subtypes which have distinct roles in immune systems. IL-10 secretion increased while CLEC7A and IL-1ra, which are M2a markers, decreased, and based on this, it was assumed that nano-GOs upregulate other M2-subtype cells. To prove this, M2a, M2b and M2c macrophages were induced, and the role of a graphene nano-structure was identified. As shown in the above-described result, the CD163 and CD206 expression of the M2a macrophages significantly decreased in the presence of nano-GOs (FIGS. 20D and 21A). In addition, the expression of marker genes CLEC7A and IL-1ra and a transcription factor IRF4 decreased (FIG. 21B). With regard to the M2c subtypes, no apparent change was made. A proportion of the M2b subtype macrophages was increased by the nano-GO treatment (FIGS. 20D and 21A). In addition, the nano-GO-treated M2b macrophages secreted excessive amounts of TNF and IL-6, and more IL-1β and IL-10 were expressed (FIGS. 20E and 20F). Such results show that nano-GOs upregulate the M2b macrophages, rather than the M2a or M2c macrophages, thereby attenuating an inflammatory response.

<Conclusion>

In the present invention, a protective effect of a nano-sized graphene derivative, that is, a graphene nano-structure, on experimental colitis and an action mechanism thereof were analyzed.

The inventors conducted a series of in vitro experiments to identify a comprehensive impact of the graphene nano-structure on innate immune cells and adaptive immune cells. A large amount of nano-GOs or GQDs was ingested by primarily isolated Th1 cells and CD14$^+$ macrophage-like cells. It is known that proinflammatory cytokines, particularly, IL-2, IL-12 and IFN-γ and a transcription factor T-bet play a critical role in the commitment of Type 1 helper T cells. Meanwhile, representative cytokines for Th2 and Treg, such as IL-4 and IL-10, and a proinflammatory cytokine IL-6 mediated inhibition of Th1 development. The graphene nano-structure exhibited an effect of regulating an immunogenic milieu, confirmed by cytokine production. In addition, it was identified that GQDs inhibited the proliferation of CD4$^+$T cells similarly to nano-GOs, but differently affect the development of Th1 cells.

Regulatory T cells protect tissue from excessive inflammation, and help a healing process of tissue by inhibiting activated immune cells. IL-10 and TGF-β1 were involved in the development, expansion and specific role of Treg. In the present invention, it was confirmed that, although not having a direct influence on cell fate, the nano-GO treatment improves colonic and splenic infiltration of regulatory T cells by increased production of IL-10 and TGF-β1, and GQD administration improves colonic infiltration of T cells.

Macrophages exhibit distinctive plasticity, and control their properties according to an environmental stimulus. Intestinal macrophages regulate homeostasis of the gut as a major regulator of immune tolerance and retain the functionality of regulatory T cells, thereby protecting tissue from an excessive immune response. In addition, alternatively-activated M2 macrophages also play a critical role in tissue recovery and a Th2 response. Therefore, it was examined how a graphene nano-structure affects macrophage polarization by treating M0, M1 and M2-type cells with nanoparticles.

As a result, it was confirmed that nano-GOs and GQDs activate M0 cells to polarize the cells to M1-type cells, and suppress M2-type cells. In addition, the nano-GO or GQD treatment induces the conversion of M1 macrophages into M2 macrophages, confirming that nano-GO or GQD can be a potential immunosuppressive drug.

In consideration that colonic Treg and M2-type macrophage infiltration increase during inflammation, it can be seen that the graphene nano-structure of the present invention plays a critical role in forming a regulatory loop of Treg and intestinal macrophages through IL-10 and TGF-β1 signaling.

The M2 macrophages are classified into at least three subtypes having various cellular properties such as gene profiles and functions mediated by production of various cytokines. Among the M2 subtypes, M2a and M2b exhibit immunoregulatory activities and induce Th2 responses, and M2c is involved in immunosuppressive capacity and tissue-remodeling. The interaction between a subtype of these macrophages and a graphene derivative has not yet been identified. In the present invention, during M1 induction, M1-like properties were reduced, but an IL-6 level inducing M2-type cells was not changed. In addition, a representative M2-related factor such as IL-10 significantly increased in the presence of nano-GOs. M2a-related genes such as CLEC7A and IL-1Ra were downregulated by the decreased expression of cell markers, and the M2c cells showed no significant change. Rather, the proportions of M2b-subtype cells and their related products were increased by nano-GO treatment. Such results show that nano-GOs are involved in increasing TLR-mediated signaling, and thus, among M2-type cells, M2b macrophages were indirectly influenced by the graphene nano-structure of the present invention, and involved in Treg migration in the colon under inflammation.

In conclusion, it was confirmed that nano-sized graphene derivatives of the present invention, specifically, nano-GOs and GQDs, have a protective effect on experimental colitis by inhibiting type 1 helper T cells and activating a regulatory loop between intestinal macrophages and regulatory T cells. Further, it was confirmed that such a therapeutic effect can be changed by the size and morphology of nanoparticles.

The invention claimed is:

1. A method of treating an inflammatory bowel disease, comprising administering a composition comprising an active ingredient for treating the inflammatory bowel disease to a subject in need thereof, and thereby treating the inflammatory bowel disease,
   wherein the active ingredient consists of nano-sized graphene oxide (nano-GO) or a graphene quantum dot (GQD),
   wherein the active ingredient is plate-shaped particles,
   and wherein the inflammatory bowel disease is selected from the group consisting of Crohn's disease and ulcerative colitis.

2. The method of claim 1, wherein symptoms of the inflammatory disease are treated by the administering of the composition and the symptoms are a shortened colon, hair loss, reduced activity, a reduced body weight, an increased bleeding index or an increased defecation index by the administration of the composition.

3. The method of claim 1, wherein the nano-GO has a thickness of 12 nm or less and an average diameter of 15 to 50 nm.

4. The method of claim 1, wherein the GQD is a particle having an average diameter of 1 to 10 nm and a thickness of 0.5 to 3 nm.

5. The method of claim 1, wherein the composition inhibits or reduces inflammation by inhibition of the expression or secretion of a proinflammatory cytokine, inhibition of myeloperoxidase activity, inhibition of Th1 differentiation or the Th1 response, promotion of T cell activity, upregulation of an M2b macrophage, or a combination thereof.

* * * * *